(12) United States Patent
Hode et al.

(10) Patent No.: US 11,773,188 B2
(45) Date of Patent: *Oct. 3, 2023

(54) CHITOSAN-DERIVED COMPOSITIONS

(71) Applicant: Immunophotonics, Inc, St. Louis, MO (US)

(72) Inventors: Tomas Hode, St. Louis, MO (US); Robert E. Nordquist, Oklahoma City, OK (US); Wei R. Chen, Edmond, OK (US); Raoul Carubelli, Oklahoma City, OK (US); Luciano Alleruzzo, Ballwin, MO (US); Peter Jenkins, Lawndale, NC (US); Kristopher Waynant, Olympia, WA (US); Joseph Raker, Delmar, NY (US)

(73) Assignee: Immunophotonics, Inc, St. Louis, MO (US)

( * ) Notice: Subject to any disclaimer, the term of this patent is extended or adjusted under 35 U.S.C. 154(b) by 103 days.

This patent is subject to a terminal disclaimer.

(21) Appl. No.: 17/397,579

(22) Filed: Aug. 9, 2021

(65) Prior Publication Data
US 2022/0017647 A1 Jan. 20, 2022

Related U.S. Application Data

(63) Continuation of application No. 16/028,221, filed on Jul. 5, 2018, now Pat. No. 11,111,316, which is a continuation-in-part of application No. 14/372,586, filed as application No. PCT/US2013/021903 on Jan. 17, 2013, now abandoned.

(60) Provisional application No. 61/588,783, filed on Jan. 20, 2012.

(51) Int. Cl.
| | |
|---|---|
| *A61K 47/68* | (2017.01) |
| *A61K 31/722* | (2006.01) |
| *A61P 35/00* | (2006.01) |
| *C08B 37/08* | (2006.01) |
| *A61K 39/395* | (2006.01) |
| *A61B 18/20* | (2006.01) |
| *A61K 41/00* | (2020.01) |
| *A61K 39/39* | (2006.01) |
| *A61N 5/06* | (2006.01) |
| *A61K 39/00* | (2006.01) |
| *A61N 5/067* | (2006.01) |

(52) U.S. Cl.
CPC .......... *C08B 37/003* (2013.01); *A61B 18/20* (2013.01); *A61K 31/722* (2013.01); *A61K 39/39* (2013.01); *A61K 39/39558* (2013.01); *A61K 41/0057* (2013.01); *A61K 41/0071* (2013.01); *A61K 47/6807* (2017.08); *A61N 5/062* (2013.01); *A61P 35/00* (2018.01); *A61K 2039/55583* (2013.01); *A61K 2039/585* (2013.01); *A61K 2039/812* (2018.08); *A61K 2039/86* (2018.08); *A61K 2039/884* (2018.08); *A61N 5/067* (2021.08); *A61N 5/0618* (2013.01); *A61N 5/0624* (2013.01); *A61N 2005/0659* (2013.01)

(58) Field of Classification Search
CPC .... C08B 37/003; A61K 31/722; A61K 39/39; A61K 47/36
See application file for complete search history.

(56) References Cited

U.S. PATENT DOCUMENTS

| | | |
|---|---|---|
| 4,424,346 A | 1/1984 | Hall et al. |
| 5,095,030 A | 3/1992 | Levy et al. |
| 5,214,036 A | 5/1993 | Allison et al. |
| 5,258,453 A | 11/1993 | Kopecek et al. |
| 5,283,225 A | 2/1994 | Neumann et al. |
| 5,314,905 A | 5/1994 | Pandey et al. |
| 5,747,475 A | 5/1998 | Nordquist et al. |
| 5,773,608 A | 6/1998 | Yen et al. |
| 5,912,000 A | 6/1999 | Podolski et al. |
| 6,316,007 B1 | 11/2001 | Nordquist et al. |
| 6,673,095 B2 | 1/2004 | Nordquist |
| 11,111,316 B2 | 9/2021 | Hode et al. |
| 2002/0022032 A1 | 2/2002 | Curry et al. |
| 2004/0047892 A1 | 3/2004 | Desrosiers et al. |
| 2004/0192646 A1 | 9/2004 | Yura et al. |
| 2005/0106153 A1 | 5/2005 | Nordouist et al. |
| 2006/0189573 A1 | 8/2006 | Nordquist et al. |
| 2010/0152430 A1 | 6/2010 | Chen et al. |
| 2011/0104305 A1 | 5/2011 | Day et al. |
| 2013/0330337 A1 | 12/2013 | Lillard, Jr. |

(Continued)

FOREIGN PATENT DOCUMENTS

| | | |
|---|---|---|
| EP | 1152013 A1 | 11/2001 |
| EP | 1498128 A1 | 1/2005 |

(Continued)

OTHER PUBLICATIONS

"Characterization of chitosan using triple detection size-exclusion chromatography and 13C-NMR spectroscopy Zitierlink+Volltex": http://nbn-resolving.de/urn:nbn:de:gbv:46-00101909-11; https//elib.suub.uni-bremen.de/peid=D00101909; URN: urn:nbn:de:gbv:46-00101909-11: Author(en): Weinhold, MirkoJahr: 2010.

(Continued)

*Primary Examiner* — Leigh C Maier
(74) *Attorney, Agent, or Firm* — Foley Hoag LLP; Lucas P. Watkins; Gretchen S. Peterson

(57) ABSTRACT

The present invention relates generally to therapeutic compositions comprising chitosan-derived compositions used in connection with methods for treating neoplasms, such as for instance, malignant lung, thyroid and kidney neoplasms, and other types of malignant neoplasms, and other medical disorders.

21 Claims, 13 Drawing Sheets

(56) References Cited

U.S. PATENT DOCUMENTS

| | | |
|---|---|---|
| 2015/0018748 A1 | 1/2015 | Hode et al. |
| 2016/0206718 A1 | 7/2016 | Har-Noy |
| 2017/0306038 A1 | 10/2017 | Brogdon et al. |
| 2019/0002594 A1 | 1/2019 | Hode et al. |
| 2020/0339706 A9 | 10/2020 | Hode et al. |
| 2022/0017647 A1 | 1/2022 | Hode et al. |

FOREIGN PATENT DOCUMENTS

| | | |
|---|---|---|
| EP | 2110131 A1 | 10/2009 |
| WO | WO-96/31237 A2 | 10/1996 |
| WO | WO-99/47162 A1 | 9/1999 |
| WO | WO-2002/030571 A2 | 4/2002 |
| WO | WO-2002/040055 A2 | 5/2002 |
| WO | WO-2013/109732 A2 | 7/2013 |

OTHER PUBLICATIONS

"Photodynamic therapy and biomedical lasers: Proceedings of the international conference on photodynamic therapy and medical laser applications," Elisiver Science Publisher, Milan June 24-27 (1992).

"Photosensitizing compounds: Their chemistry, biology and clinical use," John Wilet and Sons Ltd (1981).

"The Merck Index," 9th Edition, Library of Congress Card No. 76-2723, ONR-3, ONR-55, ONR-80 (1976).

Arca et al., "Chitosan-based systems for the delivery of vaccine antigens," Exp Rev, 8(7): 937-953 (2009).

Chen et al., "Effect of different components of laser immunotherapy in treatment of metastatic tumors in rats," Cancer Research, 62(15):4295-4299 (2002).

Chen et al., "Enhancement of Glycated Chitosan in Laser Cance Treatment," Proceedings of Spie, 5319: 80-86 (2004).

Chen et al., "Laser Immunotherapy: A Novel Treatment Modality for Metastatic Tumors," Molecular Therapy, 25: 37-43 (2003).

Chen et al., "Laser-photosensitizer assisted immunotherapy: a novel modality for cancer treatment," Cancer Letters, 115: 25-30 (1997).

Chen et al., "Photoimmunotherapy for Cancer Treatment," Journal of Environmental Pathology, Toxicology, and Oncology, 25(1-2): 281-291 (2006).

Chia et al., "Catalytic wet oxidation of lactose," Ind Eng Chem Res, 47(12):4049-4055 (2008).

Donati et al., "The aggregation of pig articular chondrocyte . . . " Biomaterials, 26:987-998 (2005).

Extended European Search Report for EP Application No. 13738505.0 dated Jan. 14, 2016.

Extended European Search Report for EP Application No. 20198582.7 dated May 10, 2021.

Garrett et al., "Anticancer threapy with checkpoint inhibotrs: what, where and when?" Trends in Pharmacological Sciences, 32(5): 308-316 (2011).

Ghendon et al., "Evaluation of properties of chitosan as an adjuvant for inactivated influenza vaccines administered parenterally," Journal of Medical Virology, 81(3): 494-506 (2009).

Guo-Quing Ying et al., "Preparation, water solubility and antioxidant activity of branched-chain chitosan derivatives," Carbohydrate Polymers, 83(4):1787-1796 (2011).

Hogan et al., "The Preparation and Sterilization of Ophthalmic Solutions," Ophthalmic Solutions, 71(6): 414-416 (1949).

Howling et al., "The effect of chitlin and chitosan on the proliferation of human skin . . . " Biomaterials, 22:2959-2965 (2001).

Il'ina et al., "Obtaining and study monosaccharide derivatives of low-molecular-weight chitosan," Appl. Biochem. Microbiol., 44(5): 551-558 (2008).

Intellectual Property Office of Singapore Search Report and Written Opinion dated May 22, 2015.

International Search Report and Written Opinion for International Application No. PCT/US2013/021903 dated Apr. 29, 2013.

Jeon et al., "Antitumor Activity of Chitosan Oligosaccharides Produced in Ultrafiltration Membrane Reactor System," Journal of Microbiology and Biotechnology, 12(3): 503-507 (2002).

Kim et al., "Mannosylated chitosan nanoparticle-based cytokine . . . " Mol Cancer Ther, 5(7):1723-1732 (2006).

Mi et al., "Synthesis and characterization of a novel glycocojugated macromolecule," Polymer, 47(12): 4348-4358 (2006).

Morrison and Boyd, "Organic Chemistry," Chapter 19, Second Edition, Library of Congress Card No. 66-25695 (1970).

Murugaiyan et al., "Levels of CD40 expression on dendritic cells dictate tumour growth or regression," British Society for Immunology, Clinical and Experimental Immunology, 149: 194-202 (2007).

Ruel-Gariepy et al., "A thermosensitive chitosan-based hydrogel for the local delivery of paclitaxel," European Journal of Pharmaceutics and Biopharmaceutics, 57: 53-63 (2004).

Sato et al., "In Vivo Drug Release and Antitumor Characteristics of Water-Soluble Conjugates of Mitomycin C with Glycol-Chitosan and N-Succinyl-Chitosan," Biol. Pharm. Bull., 19(9): 1170-117 (1996).

Sinha et al., "Nanotechnology in cancer therapeutics: bioconjugated nanoparticles for drug delivery," Mol. Canc. Ther., 6(5): 1909-1917 (2006).

Song et al., "Glycated chitosan as a new non-toxic immunological stimulant," Immunopharm Immunotox, 31(2):202-208 (2009).

Ta et al., "Injectable chitosan hydrogels for localised cancer therapy," Journal of Controlled Release, 126(3): 205-216 (2008).

Tommeraas et al., "Preparation and characterization of branched chitosans," Carbohydrate Polymers, 83(4): 1558-1564 (2011).

Vodna et al., "Chitosan Based Hydrogel Microspheres as Drug Carriers," Macromolecular Bioscience, 7:629-634 (2007).

Ying et al., "Preparation, water solubility nd antioxidant activity . . . " Carbohyd Polym, 83:1787-1796 (2011).

Zhou et al., "Immunostimulatory properties of glycated chitosan," Journal of Xray Science and Technology, 19(2): 285-292 (2011).

Zhou et al., "InCVAX—A novel strategy for treatment of late-stage, metastatic cancers through photoimmunotherapy induced tumor-specific immunity," Cancer Letters, 359: 169-177 (2015).

Zielinska et al, "Nanopharmaceuticals for Eye Administration: Sterilization, Depyrogenation and Clinical Applications," Biology, 9: 336 (8 pages)(2020).

Extended European Search Report for EP Application No. 19921164.0 dated Feb. 10, 2023.

International Preliminary Report on Patentability for International Application No. PCTUS1940292 dated Jul. 2, 2021.

International Search Report and Written Opinion for International Application No. PCTUS1940292 dated Nov. 6, 2019.

Nordquist, Robert E., et al. "Laser assisted immunotherapy (LIT) for chemotherapy-resistant neoplasms: recent case reports." Biophotonics and Immune Responses IX. vol. 8944. SPIE. 2014.

| Time (minutes) | Test Filter #1 | | | | Test Filter #2 | | | | Test Disc #3 | | | | Control Filter | | | | |
|---|---|---|---|---|---|---|---|---|---|---|---|---|---|---|---|---|---|
| | Pressure (PSIG) | | | Flow Rate (mL/min) | Pressure (PSIG) | | | Flow Rate (mL/min) | Pressure (PSIG) | | | Flow Rate (mL/min) | Pressure (PSIG) | | | Flow Rate (mL/min) | Temp (°C) |
| | Up Stream | Down Stream | Differential Pressure | | Up Stream | Down Stream | Differential Pressure | | Up Stream | Down Stream | Differential Pressure | | Up Stream | Down Stream | Differential Pressure | | |
| 1 | 57 | <1 | 56 | 2.1 | 57 | <1 | 56 | 2.2 | 57 | <1 | 56 | 3.0 | 22 | <1 | 21 | 3.0 | 26.0 |
| 60 | 57 | <1 | 56 | 2.1 | 57 | <1 | 56 | 2.2 | 57 | <1 | 56 | 3.0 | 23 | <1 | 22 | 3.0 | 26.0 |
| 300 | 57 | <1 | 56 | 1.3 | 57 | <1 | 56 | 1.5 | 57 | <1 | 56 | 3.0 | 23 | <1 | 22 | 2.0 | 26.1 |

Figure 9

CHITOSAN-DERIVED COMPOSITIONS

CROSS REFERENCE TO RELATED APPLICATIONS

The present application is a continuation of U.S. patent application Ser. No. 16/028,221, filed Jul. 5, 2018, which is a Continuation-in-Part (C-I-P) application of previously filed U.S. patent application Ser. No. 14/372,586, filed on Jul. 16, 2014, which is a 371 national phase entry from PCT application serial number PCT/US2013/021903, filed on Jan. 17, 2013 and which herein claims priority to U.S. provisional patent application Ser. No. 61/588,783, entitled "Chitosan-Derived Biomaterials and Applications Thereof" filed on Jan. 20, 2012, the entire contents of which are incorporated by reference in their entirety.

TECHNICAL FIELD

The present invention relates generally to therapeutic compositions comprising chitosan-derived compositions used in connection with methods for treating neoplasms, such as, malignant lung, breast, prostate, skin, thyroid and kidney neoplasms, and other types of malignant neoplasms, and other medical disorders.

BACKGROUND OF THE INVENTION

Chitosan is a derivative of chitin, a compound usually isolated from the shells of some crustaceans such as crab, lobster and shrimp. Chitin is a linear homopolymer composed of N-acetylglucosamine units joined by β 1→4 glycosidic bonds. Chitin, chitosan (partially deacetylated chitin) and their derivatives are endowed with interesting chemical and biological properties that have led to a varied and expanding number of industrial and medical applications. Glycated chitosan, described in U.S. Pat. No. 5,747,475 ("Chitosan-Derived Biomaterials"), which is herein incorporated by reference, is one such chitosan derivative.

Cancer can develop in any tissue of any organ at any age. Once an unequivocal diagnosis of cancer is made, treatment decisions become paramount. Though no single treatment approach is applicable to all cancers, successful therapies must be focused on both the primary tumor and its metastases. Historically, local and regional therapy, such as surgery or radiation, have been used in cancer treatment, along with systemic therapy, e.g., chemotherapy drugs. Despite some success, conventional treatments are not effective to the degree desired, and the search has continued for more efficacious therapies. There is clearly a significant unmet need for more efficient cancer therapies.

Conventional glycated chitosan preparations, as described in U.S. Pat. No. 5,747,475 ("Chitosan-Derived Biomaterials"), have shown significant efficacy as an immunoadjuvant in the treatment of metastatic tumor models in animals.

However, conventional glycated chitosan preparations, when dispersed, suspended or dissolved in aqueous solutions are often very difficult to inject or dispense in the biomedical applications to which they are put. Moreover, conventional glycated chitosan preparations, as described in U.S. Pat. No. 5,747,475 ("Chitosan-Derived Biomaterials"), are nearly impossible to sterile filter, rendering them unsuitable for industrial manufacturing according to Current Good Manufacturing Practices (cGMP), and therefore unsuitable for human use. It is thus an object of the present invention to provide improved viscoelastic glycated chitosan preparations which are far less subject to the above-noted disadvantages.

SUMMARY OF THE INVENTION

According to one embodiment, the present invention relates generally to therapeutic formulations comprising chitosan-derived compositions used in connection with methods for treating neoplasms and other medical disorders.

According to another embodiment, the present invention provides a viscoelastic glycated chitosan polymer of Formula 1:

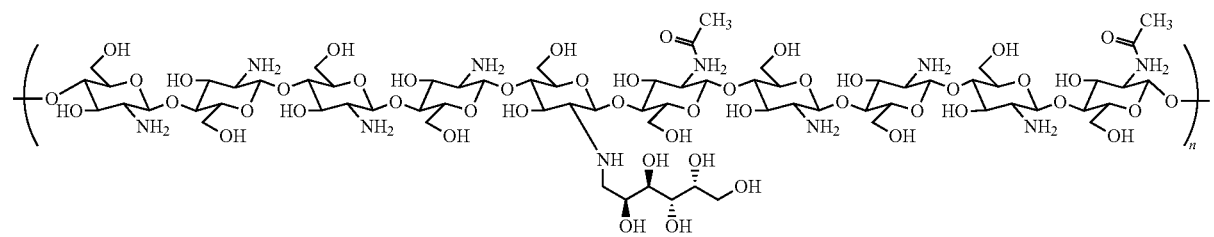

wherein:

n is an integer of from about 5 to about 6900 for a molecular weight range of 1000 to 1,500,000 Daltons; and the degree of glycation of free amino groups of the chitosan polymer ranges between about one tenth of one percent to about thirty percent.

According to another embodiment, the present invention provides an injectable pharmaceutical composition comprising: a sterile filtered aqueous mixture of the viscoelastic glycated chitosan polymer of Formula 1,

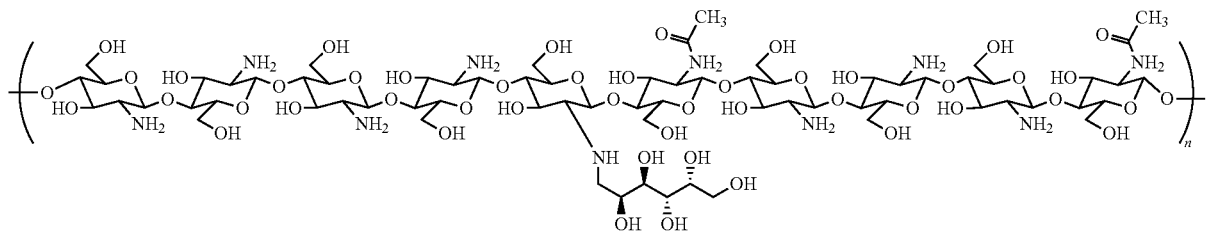

wherein: n is an integer of from about 5 to about 2300 for a molecular weight range of 1000 to less than 500,000 Daltons; and the degree of glycation of free amino groups of the chitosan polymer ranges between about one tenth of one percent to about thirty percent, in which the sterile filtered aqueous mixture has a pH from between 5 to about 7; and the sterile filtered aqueous mixture having about one percent by weight of the viscoelastic glycated chitosan polymer dissolved therein so that the sterile filtered aqueous mixture has a viscosity from about one centistokes to approximately one hundred centistokes measured at about 25 degrees Celsius.

Additional aspects and/or advantages of the invention will be set forth in part in the description which follows and, in part, may be learned by practice of the invention.

BRIEF DESCRIPTION OF THE FIGURES

These and/or other aspects and advantages of the invention will become apparent and more readily appreciated from the following description of the embodiments, taken in conjunction with the accompanying drawings of which:

FIG. 9 is a Table showing recirculation data from Study #VAL-AM-000754-B for IP-001 Drug Product (an embodiment of GC).

Figure 1:
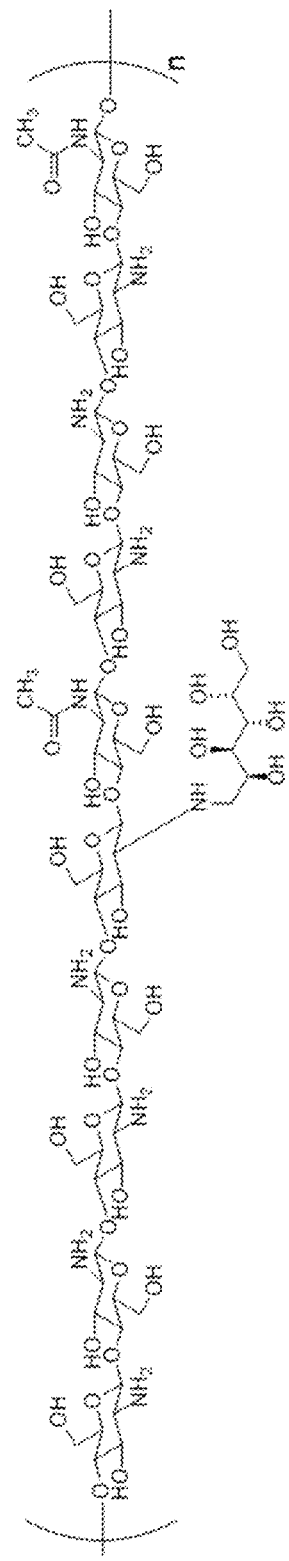
FIG. 1 depicts one conventional example of glycated chitosan, e.g., galactochitosan.

Still other objects and advantages of preferred embodiments of the present invention will become readily apparent to those skilled in this art from the following detailed description, wherein there is described certain preferred embodiments of the invention, and examples for illustrative purposes.

DETAILED DESCRIPTION

The invention relates generally to therapeutic formulations comprising chitosan-derived compositions used in connection with methods for treating neoplasms and other medical disorders. It is to be understood that all references cited herein are incorporated by reference in their entirety.

Reference will now be made in detail to certain embodiments of the present invention, examples of which are illustrated in the accompanying drawings, wherein like reference numerals refer to the like elements throughout. It is to be understood that the invention is capable of modifications in various obvious respects, all without departing from the spirit and scope of the invention. Accordingly, the description should be regarded as illustrative in nature, and not as restrictive.

Glycated Chitosan

Glycated chitosan is a product of the glycation (i.e., non-enzymatic glycosylation) of free amino groups of chitosan, followed by stabilization by reduction. Glycation endows the chitosan with advantageous solubility and viscosity characteristics which facilitate the use of the derivative in conjunction with laser-assisted immunotherapy and other applications of the derivative. The glycation of chitosan also renders the chitosan more hydrophilic whereby more water is absorbed and retained by the polymer than would otherwise be the case.

In accordance with preferred embodiments of the present invention, a chitosan-derived biomaterial comprises a linear homopolymer of deacetylated chitin (chitosan), wherein the deacetylated chitin has a number of otherwise free amino groups bonded to a carbonyl group of a reducing monosaccharide or oligosaccharide to form glycated chitosan. Glycated chitosan can thus be obtained as the reaction product between the carbonyl group of a reducing monosaccharide or oligosaccharide and the free amino groups of deacetylated chitin. Thus, the term "glycated chitosan" as used herein is intended to refer to a product of the glycation, i.e., non-enzymatic glycosylation, of free amino groups of chitosan, followed by stabilization by reduction. Generally speaking, glycation (or non-enzymatic glycosylation) is intended to refer to a process that occurs when a sugar molecule, such as fructose or glucose, binds to a substrate, such as a protein or lipid molecule, without the contributing action of an enzyme. One such example is the non-enzymatic reaction of a sugar and an amine group of a protein to form a glycoprotein.

Glycated chitosan, thus generally includes the products resulting from the reaction between the free amino groups of chitosan and the carbonyl groups of reducing monosaccharides and/or oligosaccharides. The products of this reaction, which mainly are a mixture of Schiff bases (i.e. the carbon atom from the carbonyl group is now doubly bonded to the nitrogen from the free amine releasing one molecule of water) and Amador products (i.e. the carbon atom of said carbonyl group is singly bonded to the nitrogen atom of said amino group while an adjacent carbon atom is double bonded to an oxygen atom) may be used as such or after stabilization by reduction with hydrides, such as boron-hydride reducing agents, for example $NaBH_4$, $NaBH_3CN$, $NaBH(OAc)_3$, etc, or by exposure to hydrogen in the presence of suitable catalysts.

The presence of primary and secondary alcohol groups, and of primary amino groups in chitosan, facilitate a number of approaches for chemical modifications designed mainly to achieve their solubilization and to impart special properties for specific applications.

Solubilization of chitin and chitosan can be achieved by partial hydrolysis to oligosaccharides. For chitosan, treatment with a variety of acids, both organic and inorganic, leads to the formation of water soluble chitosonium salts by protonation of the free amino groups. Additional modifications of the amino groups include the introduction of chemical groups such as carboxymethyl, glyceryl, N-hydroxybutyl and others. Glycation, i.e., non-enzymatic glycosylation of the free amino groups of chitosan, followed by stabilization by reduction, offers a preferred approach for the preparation of various pharmaceutical formulations utilized in the present invention.

For illustrative purposes, one conventional example of glycated chitosan, e.g., galactochitosan, is shown in FIG. 1, which is also described and illustrated in U.S. Pat. No. 5,747,475.

FIG. 1 is an exemplary structure of conventional glycated chitosan, where the molecular weight is approximately 1,500,000 Daltons and all amino groups are glycated.

U.S. Pat. No. 5,747,475 is very limited in its description and describes only one specific galactochitosan in terms of molecular weight; specifically, U.S. Pat. No. 5,747,475 only describes galactochitosan with a molecular weight of 1500 kDa.

Unlike the conventional 1500 kDa galactochitosan described in U.S. Pat. No. 5,747,475, it is to be clearly understood that the glycated chitosan of the present invention as described herein is intended to include glycated chitosan having a molecular weight less than 1500 kDa. Moreover, unlike conventional chitosans, the glycated chitosans of the present invention is a completely different and novel composition of matter with a number of surprisingly unexpected properties, benefits and advantages, including unexpectedly beneficial viscoelastic properties.

The glycated chitosan of the present invention is in the form of a Schiff base, an Amadori product, or preferably, in their reduced secondary amine or alcohol, respectively. In another embodiment, the glycated chitosan includes a carbonyl reactive group. It is preferred that glycated chitosan of the present invention is obtained by reacting chitosan with a monosaccharide and/or oligosaccharide, preferably in the presence of an acidifying agent, for a time sufficient to accomplish Schiff base formation between the carbonyl group of the sugar and the primary amino groups of chitosan (also referred to herein as glycation of the amino group) to a degree whereby about 0.1% to about 30% (and most preferably above 2%) glycation of the amino groups of the chitosan polymer is achieved. This is preferably followed by stabilization by reduction of Schiff bases and of their rearranged derivatives (Amadori products) to the secondary amines or alcohols.

The present invention is the first demonstration whereby about 0.1% to about 30% (and most preferably above 2%) glycation of the chitosan polymer is achieved. Contrary to the present invention, others have failed to achieve or recognize this significant result. Thus, according to a preferred embodiment, the present invention provides a viscoelastic glycated chitosan formulation, consisting essentially of glycated chitosan polymer, wherein the glycated chitosan polymer has a molecular weight between about 50,000 Daltons to about 1,500,000 Daltons, and further wherein the glycated chitosan polymer possesses from about one tenth of a percent to about thirty percent glycation of its otherwise free amino groups.

The products resulting from the non-enzymatic glycosylation of free amino groups of chitosan are thus mainly a mixture of Schiff bases, i.e. the carbon atom of the initial carbonyl group double bonded to the nitrogen atom of the amino group (also known as the imine functional group), and Amadori products, i.e. the carbon atom of the initial carbonyl group bonded to the nitrogen atom of said amino group by a single bond while an adjacent carbon atom is double bonded to an oxygen atom forming a ketone group. These products (resulting from the non-enzymatic glycosylation process) may be used as such, or after stabilization by reduction with hydrides, such as boron-hydride reducing agents, for example $NaBH_4$, $NaBH_3CN$, $NaBH(OAc)_3$, etc, or by exposure to hydrogen in the presence of suitable catalysts.

Chitosan deamination with nitrous acid can be used to generate reducing aldoses and oligosaccharides suitable for the glycation of chitosan. Deamination of the deacetylated glucosaminyl residues by nitrous acid results in the selective cleavage of their glycosidic bonds with the formation of 2,5-anhydro-D-mannose residues. Depending on the composition of specific areas of the chitosan chain, the anhydro hexose could be released as the monosaccharide, or occupy the reducing end of an oligosaccharide. Release of free N-acetylglucosamine could also occur from some regions of the chitosan chain. Similar treatment of N-deacetylated glycoproteins and glycolipids can be utilized to obtain oligosaccharides of defined chemical composition and biological activity for special preparations of glycated chitosan.

Various products obtained by chitosan glycation will be utilized as such or reacted with other natural or synthetic materials, e.g., reaction of aldehyde-containing derivatives of glycated chitosan with substances containing two or more free amino groups, such as on the side chains of amino acids rich in lysine residues as in collagen, on hexosamine residues as in chitosan and deacetylated glycoconjugates, or on natural and synthetic diamines and polyamines. This is expected to generate crosslinking through Schiff base formation and subsequent rearrangements, condensation, dehydration, etc. Stabilization of modified glycated chitosan materials can be made by chemical reduction or by curing involving rearrangements, condensation or dehydration, either spontaneously or by incubation under various conditions of temperature, humidity and pressure. The chemistry of Amadori rearrangements, Schiff bases and the Leukart-Wallach reaction is detailed in The Merck Index, Ninth Edition (1976) pp. ONR-3, ONR-55 and ONR-80, Library of Congress Card No. 76-27231, the same being incorporated herein by reference. The chemistry of nucleophilic addition reactions as applicable to the present invention is detailed in Chapter 19 of Morrison and Boyd, Organic Chemistry, Second Edition (eighth printing 1970), Library of Congress Card No. 66-26695, the same being incorporated herein by reference.

As further described herein, particular types (e.g., particular types of reducing sugars) and degrees of glycation have surprisingly been found to endow the chitosan with unexpected and advantageous solubility characteristics which facilitate the use of the glycated chitosan in conjunction with laser-assisted immunotherapy and other therapeutic applications. The glycation of chitosan also advantageously renders the chitosan more hydrophilic whereby more water is absorbed and retained by the polymer than would otherwise be the case. The D-galactose derivative of chitosan is particularly preferred insofar as D-galactose has a relatively higher naturally occurring incidence of its open chain form. The glycated chitosan may be prepared in any number of suitable formulations including, for example, a powder form, as a viscous formulation, or in any other suitable form.

In accordance with other preferred embodiments of the invention, chitosan may be non-enzymatically glycated utilizing any of a number of the same or different reducing sugars, e.g., the same or different monosaccharides and/or oligosaccharides. Examples of such monosaccharide glycosylation agents are the more naturally occurring D-trioses, D-tetroses, D-pentoses, D-hexoses, D-heptoses, and the like, such as D-glucose, D-galactose, D-fructose, D-mannose, D-allose, D-altrose, D-Idose, D-talose, D-fucose, D-arabinose, D-gulose, D-hammelose, D-lyxose, D-ribose, D-rhamnose, D-threose, D-xylose, D-psicose, D-sorbose, D-tagatose, D-glyceraldehyde, dihydroxyacetone, D-erythrose, D-threose, D-erythrulose, D-mannoheptulose, D-sedoheptulose and the like. Suitable oligosaccharides include the fructo-oligosaccharides (FOS), the galacto-oligosaccharides (GOS), the mannan-oligosaccharides (MOS) and the like.

Preferred Viscoelastic Properties

Conventionally produced chitosan products, when dispersed, suspended or dissolved in aqueous solutions are very difficult to produce according to GMP standards, and have a number of disadvantages in terms of administration and other uses.

Preferred embodiments of the present invention overcome the long unmet needs for improved therapeutic chitosan products by providing improved viscoelastic glycated chitosan preparations which are not subject to the disadvantages of conventional approaches.

The term "viscoelastic" as used herein refers to the viscosity of a particular composition, preparation or formulation. Viscosity is well understood as a measure of the resistance of a fluid which is being deformed by either shear stress or tensile stress. In other words, viscosity describes a fluid's internal resistance to flow and may be thought of as a measure of fluid friction.

a. Unexpected Improvements in Injectability of GC Preparations

It has been surprisingly and unexpectedly discovered that the injectability of formulations of glycated chitosan (GC), for instance solutions or suspensions, is nonobviously dependent upon the viscosity and rheological properties of the GC. These properties are, in turn, highly dependent upon the molecular weight of the GC, the degree of polymerization of the chitin parent to the chitosan, the degree of deacetylation of the chitin parent, and the degree of glycation of the chitosan. These latter properties determine the degree of entanglement of the polymer chains of the GC as well as the degree of intramolecular hydrogen bonding occasioned by the number and nature of the substituents present on the GC molecule (i.e., acetyl and saccharide), both of which contribute significantly to the viscosity and other rheological properties of solutions prepared therefrom.

It has been surprisingly and unexpectedly discovered that the improved viscoelastic glycated chitosan preparations of the present invention possess numerous advantages, for instance, (i) administration of a non-toxic preparation for treatment of neoplasm in a patient; (ii) far superior injectability (e.g., through different gauge needles) in a clinical setting as compared to conventional treatments; (iii) improved sterile filtration of the viscoelastic preparations; and (iv) a less painful and thus an improved treatment option for patients. The term "injectability" as used herein refers to the ease with which a formulation or preparation, for instance, a formulation comprising glycated chitosan (GC), is injected into a subject.

According to one preferred embodiment, the invention provides an injectable viscoelastic preparation comprising approximately 1 percent by weight of the above-described glycated chitosan dispersed, suspended or dissolved in an aqueous solution.

Preferred embodiments of the invention include preparations of glycated chitosan, including for instance solutions or suspensions, that have a viscosity that renders the preparations readily injectable via a needle with a relatively large needle gauge (G), thus reducing pain and discomfort for the subject. Preferred examples of relatively large gauge needles include needles that have the following dimensions: a nominal inner diameter of from about 0.337 mm (23 G) to about 0.210 mm (27 G).

According to one example, a viscoelastic glycated chitosan preparation is administered via injection using an injection needle having a diameter of about 20 G to about 22 G, and an effective length of a tube of the injection needle is about 1,000 mm or more such that the inflow rate of the injectable preparation, when injected at a pressure of about two to about three atmospheres through said injection needle, ranges from about 0.05 ml/second to 0.1 ml/second. According to another example, a viscoelastic glycated chitosan preparation can also be administered via injection using an injection needle having a diameter of about 25 G to about 27 G. It is also to be understood that a viscoelastic glycated chitosan preparation according to the present invention can also be administered using any other suitable gauge needle or instrument.

It has been surprisingly found that the viscoelastic glycated chitosan preparations of the present invention, for instance, solutions or suspensions, are injectable at a relatively wide range of concentrations through catheters or needles of the most commonly used gauges.

It has also been discovered that these improved viscoelastic glycated chitosan preparations (i.e., by improving the viscosity and rheological properties of the glycated chitosan compositions) also unexpectedly improve the overall ease of administration of the preparation to a subject; the efficiency of administration by the individual administering the formulation (for example, nurse, physician, or other healthcare practitioner), and the compliance and efficacy of the glycated chitosan formulations may also be enhanced.

b. Unexpected Improvements in Manufacturing and Filtration

It has also been surprisingly found that sterile filtration is unexpectedly improved using the improved viscoelastic glycated chitosan preparations of the present invention. Conventional glycated chitosan preparations, as described in U.S. Pat. No. 5,747,475 ("Chitosan-Derived Biomaterials"), was shown to be very difficult to sterile filter through a 0.22 um sterile filter, which renders it unsuitable for commercial cGMP manufacturing. In contrast, the improved viscoelastic glycated chitosan, which was discovered to have nonobvious rheological properties, was shown to be highly suitable for sterile filtration, cGMP manufacturing, and human use.

Furthermore, it has been surprisingly found that diafiltration and ultrafiltration is unexpectedly improved using the improved viscoelastic glycated chitosan preparations of the present invention. Conventional glycated chitosan preparations were difficult to diafilter and ultrafilter, causing the filter to clog, thus rendering it unsuitable for commercial cGMP manufacturing. The improved viscoelastic glycated chitosan, on the other hand, was highly suitable for diafiltration and ultrafiltration, thus significantly improving the manufacturing process.

Exemplary Methods for Determination of Viscosity

Any number of suitable techniques in the chemical arts can be used to reliably and accurately determine viscosity of a glycated chitosan formulation.

It is to be understood that viscosity can be reliably measured with various types of instruments, e.g., viscometers and rheometers. A rheometer is used for those fluids which cannot be defined by a single value of viscosity and therefore require more parameters to be set and measured than is the case for a viscometer. Close temperature control of the fluid is essential to accurate measurements, particularly in materials like lubricants, whose viscosity can double with a change of only 5° C.

In accordance with the present invention, the viscosity of a glycated chitosan preparation can be determined according to any suitable method known in the art.

For instance, viscosity can be reliably measured in units of centipoise. The poise is a unit of dynamic viscosity in the centimeter gram second system of units. A centipoise is one one-hundredth of a poise, and one millipascal-second (mPa·s) in SI units (1 cP=$10^{-2}$ P=$10^{-3}$ Pa·s). Centipoise is properly abbreviated cP, but the alternative abbreviations cps, cp, and cPs are also commonly seen. A viscometer can be used to measure centipoise. When determining centipoise, it is typical that all other fluids are calibrated to the viscosity of water.

Exemplary Determination of Viscosity of Glycated Chitosan Preparations

There are numerous factors that affect the viscosity of solutions and, in particular, solutions of polymers, other than molecular weight. In the case of glycated chitosan (GC) the injectability of solutions of GC is highly dependent upon the viscosity and rheological properties of the GC in solution. These properties are, in turn, highly dependent upon the molecular weight of the GC, the degree of polymerization of the chitin parent to the chitosan, the degree of deacetylation of the chitin parent, and the degree of glycation of the chitosan. These latter properties determine the degree of entanglement of the polymer chains of the GC as well as the degree of intramolecular hydrogen bonding occasioned by the number and nature of the substituents present on the GC molecule (i.e., acetyl and saccharide), both of which contribute significantly to the viscosity of solutions prepared therefrom.

It has been surprisingly discovered that the improved viscosity and rheological properties of glycated chitosan preparations are, in turn, highly dependent upon particular physiochemical properties of the glycated chitosan. The term "physiochemical property" as used herein is intended to include, but is not limited to, any physical, chemical or physical-chemical property of a molecular structure, such as glycated chitosan. As described further herein, a few examples of these physiochemical properties are:

(i) the molecular weight of the glycated chitosan;

(ii) the degree of polymerization of the chitin parent to the chitosan;

(iii) the degree of deacetylation of the chitin parent; and (iv) the degree of glycation of the chitosan.

Structural Formula 1

Figure 2:
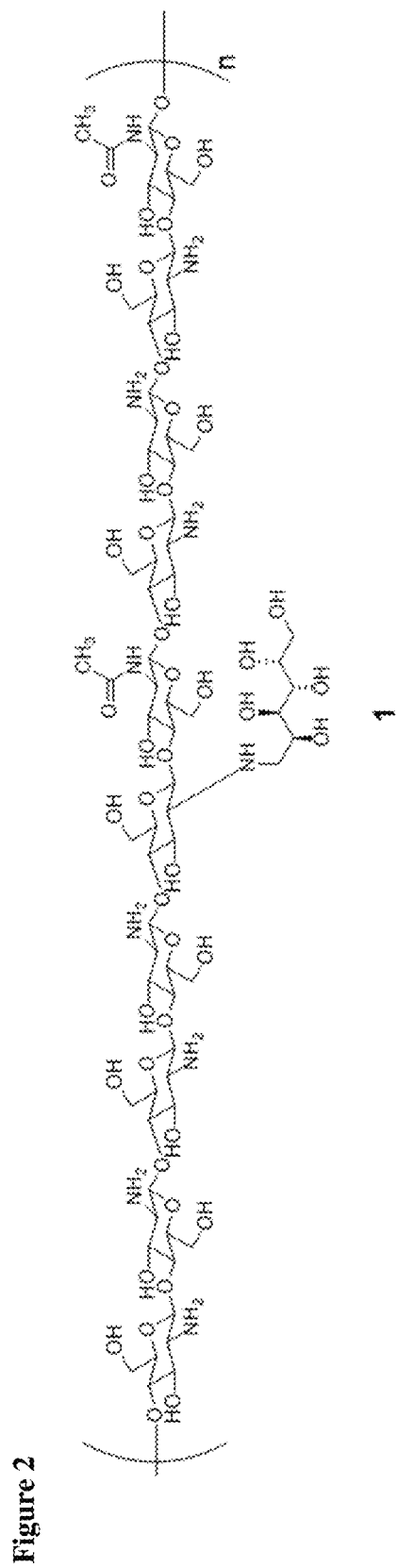
FIG. 2 depicts one exemplary structure of viscoelastic glycated chitosan of the present invention, where the deacetylation of the parent chitosan is 80%, and the glycation of total available deacetylated amino groups is 12.5%.

In one embodiment, there is provided a viscoelastic glycated chitosan of Formula 1, as illustrated in FIG. 2:

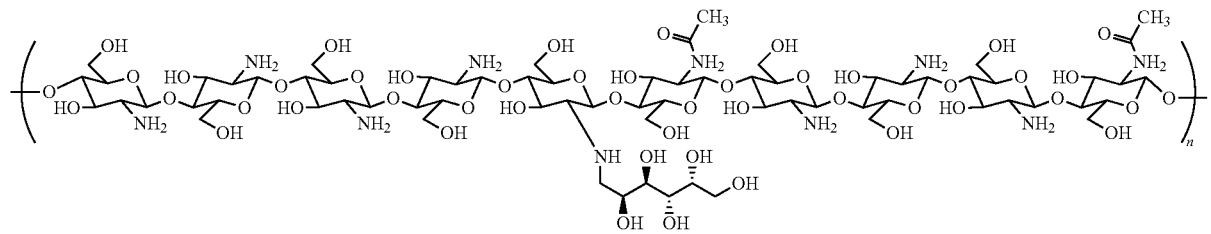

Formula 1 includes ten monomeric units, one of which being galactated, representing, in one example, 12.5% galactation. In one example, where 5% galactation is present, the integer "n" ranges from about 5 to about 6900, which represents a molecular weight range of 1000 to 1,500,00 daltons. For a 250 kDa chain, there would be 1150 monomers. Given that the formula represents a semisynthetic biopolymer, the person of ordinary skill in the art will readily understand that the molecular weights are given as an average because in any formulation, there will be polymer chains of larger and smaller chain length. In one specific example, there is provided a viscoelastic glycated chitosan where the molecular weight is approximately 250 kDa, where the deacetylation of the parent chitosan is about 80%, and the glycation of total available deacetylated amino groups is about 12.5%. Specifically, in a preferred embodiment the molecular weight of the viscoelastic glycated chitosan is less than 500,000 Daltons.

(i) Molecular Weight of the Glycated Chitosan

Any number of suitable techniques in the chemical arts can be used to reliably and accurately determine the molecular weight (MW) of the glycated chitosan.

It is preferred that a viscoelastic glycated chitosan preparation is prepared as an injectable formulation comprising glycated chitosan with a molecular weight (MW) less than about 1500 kDa. Examples of preferred viscoelastic glycated chitosan preparations comprise glycated chitosan with a molecular weight (MW) of between about 50 Kilodaltons (kDa) and about 1500 kDa. Specifically, in a preferred embodiment the molecular weight is less than 500,000 Daltons.

In certain embodiments, a viscoelastic glycated chitosan preparation comprises glycated chitosan with a molecular weight (MW) of between about 100 kDa and about 1000 kDa; and more preferably, between about 100 kDa and about 300 kDa. Specifically, in a preferred embodiment the molecular weight is less than 500,000 Daltons.

In certain specific embodiments, n is an integer of from about 5 to about 6900 for a molecular weight range of 1000 to 1,500,000 Daltons. In one example, the viscoelastic glycated chitosan polymer has a molecular weight between about 50,000 Daltons to about 1,500,000 Daltons. In another example, the viscoelastic glycated chitosan polymer has a molecular weight between about 190,000 Daltons to about 310,000 Daltons. In yet another example, the viscoelastic glycated chitosan polymer, the molecular weight is approximately 250,000 Daltons. Specifically, in a preferred embodiment the molecular weight is less than 500,000 Daltons.

Various techniques can be used to accurately determine molecular weight.

The invention encompasses chitosan-derived compositions comprising derivatives of chitosan which are water-soluble or water-dispersible. In accordance with the present invention, it has also been surprisingly found that in certain embodiments, with increasing molecular weight (MW), more water is required to solubilize the glycated chitosan (GC). This in turn means less amount of the water is "free", i.e. not hydrogen-bonded to the GC (assuming no additional water is added to the solution), which in itself contributes to higher viscosity. As shown in example 3 below, this result has been unexpectedly found to add to the viscosity increase that is given by the increasing size of the molecule, giving an exponential (or something similar), rather than a linear relationship between viscosity and MW (when concentration is compensated for).

(ii) Degree of Polymerization (DP) of the Chitin Parent to the Chitosan

The degree of polymerization (DP) of the chitin parent to the chitosan can be reliably and accurately determined according to any number of suitable methods or techniques known in the chemical arts.

In one approach, it is preferred that the degree of polymerization (DP) is determined by dividing the molecular weight of the chitosan by the molecular weight of the glucosamine link.

(iii) Degree of Deacetylation of the Chitin Parent

Another physiochemical property is the degree of deacetylation of the chitin parent. Any number of suitable techniques in the chemical arts can be used to reliably and accurately determine the degree of deacetylation of the chitin parent.

NMR is one technique that can be used to determine the degree of deacetylation of chitin or chitosan.

(iv) Degree of Glycation of the Chitosan

Any number of suitable techniques in the chemical arts can be used to reliably and accurately determine the degree of glycation of the chitosan.

NMR is one technique that can be used to detect and measure the bonding of monosaccharides and/or oligosaccharides to the chitosan polymer.

C/N elemental combustion analysis is another technique that can be used to determine the percent glycation of the glycated chitosan by means of comparing the C/N ratio of glycated chitosan vs. the parent chitosan.

Enzymatic digestion coupled with HPLC is yet another technique that can be used to determine percent glycation.

It is to be understood that other suitable analytical methods and instrumentation can also be used for simultaneous detection, measurement and identification of multiple components in a sample, e.g., for simultaneous detection, measurement and identification of glycated and non-glycated chitosan in a sample.

Colorimetric measurement of chemicals bound to remaining free amino groups, such as via a ninhydrin reaction, can be used to assess the degree of glycation.

It has thus been found that glycated chitosans having preferred molecular weights, degrees of polymerization of the chitin parent to the chitosan, degrees of deacetylation of the chitin parent, and degrees of glycation of the chitosan enable improved preparation of glycated chitosan solutions which are injectable at a relatively wide range of concentrations of the glycated chitosan through catheters or needles of commonly used gauges.

Preferred Methods of Preparing Glycated Chitosan

Still other embodiments of the invention relate to methods for the preparation of glycated chitosan formulations. Glycated chitosan is preferably obtained by reacting chitosan with a monosaccharide and/or oligosaccharide, preferably in the presence of an acidifying agent, for a time sufficient to accomplish Schiff base formation between the carbonyl group of the sugar and the primary amino groups of chitosan (also referred to herein as glycation of the amino group) to a degree whereby at least some percentage (for example, two percent or higher) glycation of the chitosan polymer is achieved. This is preferably followed by stabilization by reduction of Schiff bases and of their rearranged derivatives (Amadori products) to their secondary amines or alcohols, respectively. NMR tracings can be used to verify the bonding of the monosaccharides and/or oligosaccharides to the chitosan polymer, whereas chemical measurement of remaining free amino groups, such as via a ninhydrin reaction, can be used to assess the degree of glycation.

In preferred embodiments, conditions can be adjusted as needed to improve desired results during the manufacture of glycated chitosan. For instance, it has been unexpectedly discovered, in accordance with the present invention, that improvements in the manufacture of glycated chitosan can be achieved by controlling the pH conditions, as described for instance in Example 4.

According to one example of preparation of glycated chitosan for use in the present invention, approximately three grams of a reducing monosaccharide (e.g., glucose, galactose, ribose), or an equivalent amount of a reducing oligosaccharide, is dissolved in 100 ml of distilled water under gentle magnetic stirring in an Erlenmeyer flask. Then approximately one gram of chitosan is added, and thereafter suitable process steps can then be performed to yield the glycated chitosan preparation with desired viscoelastic properties and with desired purity characteristics.

One exemplary method for industrial-scale production of chitosan Involves the following four steps: demineralization (DM), deproteinization (DP), decoloration (DC) and deacetylation (DA). Chitin extraction from, e.g., crustacean shells is carried out by an alkali-acid treatment. Samples are deproteinized by treating with alkaline formulation, demineralized with acid and decolorized with organic solvent (e.g., acetone), followed by bleaching (with, e.g., sodium hypochlorite). Chitin deacetylation is carried out using, e.g., sodium hydroxide formulation. The degree of polymerization of chitosan is adjusted by depolymerization; the most convenient procedures being (1) nitrous acid degradation in deuterated water. The reaction is selective, stoichiometric with respect to GlcN, rapid, and easily controlled, (2) depolymerization by acid hydrolysis, or (3) enzymatic degradation with a commercial preparation (Pectinex Ultra Spl). The enzymatic method yields shorter fragments with a higher proportion of fully deacetylated chitooligomers. Conversely, acid hydrolysis of the starting chitosan results in fragments with degrees of polymerization up to sixteen and more monoacetylated residues than with the enzymatic procedure.

Polymerized Glycated Amino-Sugars

As described herein, chitosan (partially deacetylated chitin) is a derivative of chitin (a linear homopolymer composed of N-acetylglucosamine units joined by β 1→4 glycosidic bonds). Chitosan-derived compositions thus comprise a homopolymer of partially deacetylated chitin, wherein the partially deacetylated chitin has a number of otherwise free amino groups bonded to a carbonyl group of a reducing monosaccharide or oligosaccharide creating an imine bond (Schiff Base) or related product (Amadori Rearrangement) and releasing one molecule of water.

Since chitin and chitosan are polymers of glucosamine, the present invention also contemplates non-enzymatically glycated glucosamine, e.g., glycated glucosamine monomers, or glycated glucosamine units. In other words, the present invention also contemplates non-enzymatic glycation of amino-sugar monomers in general.

For instance, one example is a glycated glucosamine wherein the N-substituent is a galactose. It is preferred that glycation of glucosamine monomers is performed after at least a percentage of the glucosamine monomers are initially deacetylated.

Moreover, the present invention also contemplates (1) polymers of glycated glucosamine units (polymerized glycated amino-sugars), (2) combination polymers of glycated and non-glycated glucosamines, and (3) combinations of glycated and non-glycated glucosamine polymers wherein:

i) the percentage of non-deacetylated glucosamine monomers is from about 1% to about 30%;

ii) the degree of polymerization (of the various combinations of deacetylated, non-deacetylated, glycated and non-glycated glucosamine units) is from about $x_n$=300 to about $x_n$=8000, most preferably about $x_n$=1500; and/or iii) the percent glycation of the free amino groups of the deacetylated polymerized glucosamine is from about 0.1% to about 30%.

The present invention also contemplates uses of polymerized glycated glucosamine polymers that are the same or similar to uses of glycated chitosan. These include, for instance, immunoadjuvant properties and uses, e.g., in the context of in situ cancer vaccines (inCVAX) such as laser-assisted immunotherapy (LIT).

Exemplary Formulations and Applications

Examples of various types of pharmaceutically acceptable formulations or preparations that can be used in accordance with the present invention include, for instance, solutions, suspensions, and other types of liquid or semi-liquid formulations for injectability of the viscoelastic glycated chitosan preparations. For instance, the pharmaceutically acceptable formulations or preparations may include glycated chitosan dispersed, suspended or dissolved in substantially aqueous formulations. By use of the term "substantially aqueous" it is to be understood that the formulations or preparations, in certain embodiments, may include some percentage of one or more non-aqueous components, and one or more pharmaceutically acceptable excipients.

According to one example, a viscoelastic preparation is preferably formulated as an aqueous solution possessing a pH from between about 5.0 to about 7.

A viscoelastic preparation can also be formulated as an aqueous solution comprising a buffered physiological saline solution consisting essentially of glycated chitosan.

A viscoelastic preparation can also be formulated consisting essentially of glycated chitosan polymer, wherein the glycated chitosan polymer possesses from about one tenth (0.1) of a percent to about thirty (30) percent glycation of its otherwise free amino groups.

According to a specific example, the glycated amino groups are present from about one tenth of one percent to less than thirty percent of available amino groups. According to another example, the viscoelastic glycated chitosan polymer includes glycated amino groups present from 1% to 8% of available amino groups. In yet another example, the viscoelastic glycated chitosan polymer includes glycated amino groups present from 3 to 6% of available amino groups. In still another example, the viscoelastic glycated chitosan polymer includes glycated amino groups present from about 0.5% to about 9.5% of available amino groups, In another embodiment, a viscoelastic preparation can be formulated consisting essentially of glycated chitosan (GC) polymer, wherein the glycated chitosan polymer possesses about two (2) percent glycation of its otherwise free amino groups.

In another embodiment, a viscoelastic preparation can be formulated consisting essentially of glycated chitosan polymer, wherein the glycated chitosan polymer has a molecular weight between about 50,000 to about 1,500,000 Daltons. Specifically, in a preferred embodiment the molecular weight is less than 500,000 Daltons.

Another example includes a viscoelastic GC preparation comprising about one (1) percent by weight of a glycated chitosan polymer dispersed in an aqueous solution, said aqueous solution having a viscosity of between about one (1) to about one hundred (100) centistokes measured at about 25 degrees Celsius.

Yet another example includes an aqueous solution having about one percent by weight of glycated chitosan and from about one tenth (0.1) of a percent to about thirty (30) percent glycation of otherwise free amino groups of said glycated chitosan, wherein the aqueous solution has a viscosity from about one (1) centistokes to approximately one hundred (100) centistokes.

In yet another embodiment, a viscoelastic preparation can be formulated consisting essentially of glycated chitosan polymer, comprising about or above one percent by weight of the glycated chitosan polymer dispersed in an aqueous solution, wherein the glycated chitosan polymer possesses about two (2) percent glycation of its otherwise free amino groups, and wherein the aqueous solution has a viscosity suitable for ease of injectability and administration to a subject.

In yet another embodiment, a viscoelastic preparation can be formulated consisting essentially of glycated chitosan polymer, additionally containing one or more different viscoelastic materials miscible in an aqueous solution. Examples of suitable viscoelastic materials include, but are not limited to, hyaluronic acid, chondroitin sulfate and carboxymethylcellulose.

The viscoelastic preparation can include glycated chitosan polymer comprising a monosaccharide bonded to an otherwise free amino group. The glycated chitosan polymer can take any suitable form, such as a Schiff base, an Amadori product or mixtures thereof. The glycated chitosan polymer can also be in the form of a reduced Schiff base (secondary amine), a reduced Amadori product (alcohol) or mixtures thereof.

The viscoelastic preparation can also be formulated wherein the glycated chitosan polymer possesses a number of chemically modified monosaccharide or oligosaccharide substituents. In one embodiment, the monosaccharide comprises galactose.

The inventive formulations or preparations preferably also contain glycated chitosan in a physiologically compatible carrier. "Physiologically compatible" as used herein is to be understood to refer to materials which, when in contact with tissues in the body, are not harmful thereto. The term is intended in this context to include, but is not limited to, aqueous formulations (e.g., solutions) which are approximately isotonic with the physiological environment of interest. Non-isotonic formulations (e.g., solutions) sometimes may also be clinically useful such as, for example dehydrating agents. Additional components of the inventive solutions may include various salts such as, for instance, NaCl, KCl, $CaCl_2$, $MgCl_2$ and Na based buffers.

The above and other objects are realized by the present invention, certain preferred embodiments of which relate to glycated chitosan preparations having particular physiochemical properties that confer unexpected and surprisingly beneficial properties.

The present invention also encompasses a wide range of uses of viscoelastic glycated chitosan preparations that have surprising and unexpected properties as immunoadjuvants, for instance, in connection with in situ autologous cancer vaccines, such as laser-assisted immunotherapy for cancer, as described further herein.

Preferred embodiments of the invention provide immunoadjuvants comprising an injectable viscoelastic preparation. It is thus another object of the present invention to provide improved viscoelastic glycated chitosan preparations for other therapeutic applications, including therapeutic use as an immunoadjuvant and immunomodulator.

The present invention also encompasses various routes of administering the viscoelastic glycated chitosan immunoadjuvant formulations, such as via injection. In a preferred approach, the immunoadjuvant is preferably prepared as a formulation for injection into or around the tumor mass. It should be recognized however that other methods may be sufficient for localizing the immunoadjuvant in the tumor site. One such alternative delivery means is conjugation of the immunoadjuvant to a tissue specific antibody or tissue specific antigen, such that delivery to the tumor site is enhanced. Any one method, or a combination of varying methods, of localizing the immunoadjuvant in the tumor site is acceptable so long as the delivery mechanism insures sufficient concentration of the immunoadjuvant in the neoplasm.

According to certain preferred embodiments, the present invention provides for various pharmaceutical formulations comprising viscoelastic glycated chitosan used in connection with in situ autologous cancer vaccines (inCVAX), such as laser-assisted immunotherapy, photodynamic cancer therapy (PDT) and/or other tumor immunotherapy methods, as described in further detail herein. It has been observed that it is desirable to utilize glycated chitosan preparations having a suitable viscosity that enables their use as an injectable or other formulation as an immunoadjuvant in applications such as inCVAX and/or PDT and/or tumor immunotherapy methods. Such applications typically involve injection of the viscoelastic glycated chitosan formulation into the corpus of a patient. The term "immunoadjuvant" as used herein is intended to refer to any molecule, composition or substance that acts to enhance the immune system's response to an antigen; for instance, glycated chitosan which acts to enhance the immune system's response to a tumor antigen.

The immunoadjuvant composition can further include a tumor specific antibody conjugated to the glycated chitosan. The immunoadjuvant composition can also include a tumor specific antigen conjugated to the glycated chitosan. The glycated chitosan can further include a carbonyl reactive group.

According to one preferred embodiment, the present invention provides an immunoadjuvant formulation that includes a suspension or a solution of viscoelastic glycated chitosan. The viscoelastic glycated chitosan is in this preferred embodiment used in connection with photothermal treatment of a neoplasm without the use of a chromophore, where the light energy is delivered directly to the neoplasm. The light energy can be delivered topically if the neoplasm is accessible on the tissue surface (for example melanoma), or is exposed by means of surgery. The light energy can also be delivered to the neoplasm by means of fiberoptics, for example if the neoplasm is present below the tissue surface (for example breast cancer) and is not exposed through surgery.

According to another embodiment, and as described in further detail herein, the immunoadjuvant formulations of the present invention can further include a suitable chromophore. The selection of an appropriate chromophore is largely a matter of coordination with an acceptable laser wavelength of radiation. The wavelength of radiation used must, of course, be complementary to the photoproperties (i.e., absorption peak) of the chromophore. Other chromophore selection criteria include ability to create thermal energy, to evolve singlet oxygen and other active molecules, or to be toxic in their own right such as cis-platinin. In the present invention, a preferred wavelength of radiation is 805.+/−0.10 nm. The desired chromophores have strong absorption in the red and near-infrared spectral region for which tissue is relatively transparent. Another advantage of this wavelength is that the potential mutagenic effects encountered with UV-excited sensitizers are avoided. Nevertheless, wavelengths of between 150 and 2000 nm may prove effective in individual cases. The preferred chromophore is indocyanine green. Other chromophores may be used, however, their selection being based on desired photophysical and photochemical properties upon which photosensitization efficiency and photocytotoxicity are dependent. Examples of alternative chromophores include, but are not limited to, single walled carbon nanotubes (SWNT), buckminsterfullerenes ($C_{60}$), indocyanine green, methylene blue, DHE (polyhaematoporphrin ester/ether), mm-THPP (tetra(meta-hydroxyphenyl)porphyrin), $AlPcS_4$ (aluminium phthalocyanine tetrasulphonate), ZnET2 (zinc aetio-purpurin), and Bchla (bacterio-chlorophyll .alpha.).

In one embodiment, the immunoadjuvant composition is formulated as a solution or suspension. The solution or suspension can include, for instance, about 0.25% by weight of a chromophore and about 1% by weight of the glycated chitosan.

According to another preferred embodiment, the present invention provides a composition for use in conditioning a neoplasm for tandem photophysical and immunological treatment, comprising an immunoadjuvant, wherein the immunoadjuvant is conjugated to a tumor specific antigen, and wherein the immunoadjuvant is glycated chitosan.

According to still another embodiment, the present invention provides a composition for use in conditioning a neoplasm for tandem photophysical and immunological treatment, comprising a combination of a chromophore and an immunoadjuvant, wherein the chromophore and the immunoadjuvant are conjugated to a tumor specific antigen, and wherein the immunoadjuvant is glycated chitosan.

According to another preferred embodiment, the present invention provides a composition for use in conditioning a neoplasm for tandem photophysical and immunological treatment, comprising an immunoadjuvant, wherein the immunoadjuvant is conjugated to a tumor specific antibody, and wherein the immunoadjuvant is glycated chitosan. The immunoadjuvant can, in certain instances, consist essentially of glycated chitosan. The glycated chitosan can also further include a carbonyl reactive group.

According to another embodiment, the present invention provides a composition for use in conditioning a neoplasm for tandem photophysical and immunological treatment, comprising a combination of a chromophore and an immunoadjuvant, wherein the chromophore and the immunoadjuvant are conjugated to a tumor specific antibody, and wherein the immunoadjuvant is glycated chitosan. The immunoadjuvant can, in certain instances, consist essentially of glycated chitosan. The glycated chitosan can also further include a carbonyl reactive group.

The present invention thus provides injectable formulations for conditioning a neoplasm for tandem photophysical and immunological treatment, that in certain instances may include a combination of, or a mixture of, a chromophore and an immunoadjuvant, wherein the immunoadjuvant is glycated chitosan.

A composition may furthermore be prepared for use in conditioning a neoplasm for tandem photophysical and immunological treatment, comprising an immunoadjuvant, wherein the immunoadjuvant is conjugated to a tumor specific antigen, and wherein the immunoadjuvant is viscoelastic glycated chitosan with a molecular weight (MW) of between about 100 kDa and about 1000 kDa; and more preferably, between about 100 kDa and about 300 kDa. Specifically, in a preferred embodiment the molecular weight is less than 500,000 Daltons.

A composition may also be prepared for use in conditioning a neoplasm for tandem photophysical and immunological treatment, comprising a combination of a chromophore and an immunoadjuvant, wherein the chromophore and the immunoadjuvant are conjugated to a tumor specific antigen, and wherein the immunoadjuvant is viscoelastic glycated chitosan with a molecular weight (MW) of between about 100 kDa and about 1000 kDa; and more preferably, between about 100 kDa and about 300 kDa. Specifically, in a preferred embodiment the molecular weight is less than 500,000 Daltons.

Furthermore, an injectable solution may be prepared for conditioning a neoplasm for tandem photophysical and immunological treatment comprising an immunoadjuvant wherein the immunoadjuvant is viscoelastic glycated chitosan with a molecular weight (MW) of between about 100 KDa and about 1000 kDa; and more preferably, between about 100 kDa and about 300 kDa. Specifically, in a preferred embodiment the molecular weight is less than 500,000 Daltons.

An injectable solution may also be prepared for conditioning a neoplasm for tandem photophysical and immunological treatment comprising a mixture of a chromophore and an immunoadjuvant wherein the immunoadjuvant is viscoelastic glycated chitosan with a molecular weight (MW) of between about 100 kDa and about 1000 kDa; and more preferably, between about 100 kDa and about 300 kDa. Specifically, in a preferred embodiment the molecular weight is less than 500.000 Daltons.

In one example, the viscoelastic glycated chitosan compositions of the present invention is used as an immunoadjuvant in a novel cancer treatment. Photothermal and immunological therapies are combined by irradiating the neoplasm directly to the tumor without the use of a chromophore, and subsequently introducing the chitosan-derived immunoadjuvant into or around the irradiated neoplasm. Following the application of a laser with irradiance sufficient to induce neoplastic cellular destruction, cell-mediated and humoral immune responses to the neoplastic antigens thus released are stimulated (enhanced) by the immunoadjuvant component.

In another example, photodynamic and immunological therapies are combined by introducing both a chromophore and a chitosan-derived immunoadjuvant (also called immuno-modulator or immunopotentiator) into a neoplasm. Upon application of a laser with irradiance sufficient to induce neoplastic cellular destruction, cell-mediated and humoral immune responses to the neoplastic antigens thus released are stimulated (enhanced) by the immunoadjuvant component.

The chromophore and immunoadjuvant may be combined into a solution for injection into the center of the tumor mass or injected separately into the tumor mass. It should be recognized however that other methods may be sufficient for localizing the chromophore and immunoadjuvant in the tumor site. One such alternative delivery means is conjugation of the chromophore or immunoadjuvant or both to a tissue specific antibody or tissue specific antigen, such that delivery to the tumor site is enhanced. Any one method, or a combination of varying methods, of localizing the chromophore and immunoadjuvant in the tumor site is acceptable so long as the delivery mechanism insures sufficient concentration of the components in the neoplasm.

According to another embodiment, a method for treating a neoplasm in a human or other animal host, comprises: (a) selecting an immunoadjuvant, wherein the immunoadjuvant comprises viscoelastic glycated chitosan; (b) irradiating the conditioned neoplasm whereby neoplastic cellular destruction of the conditioned neoplasm is induced producing fragmented neoplastic tissue and cellular molecules; and (c) introducing the immunoadjuvant into or around the neoplasm, which stimulates the self-immunological defense system of the host to process the fragmented neoplastic tissue and cellular molecules, such as tumor antigens, and thus create an immunity against neoplastic cellular multiplication.

According to yet another embodiment, a method for treating a neoplasm in a human or other animal host, comprises: (a) selecting a chromophore and an immunoadjuvant, wherein the immunoadjuvant comprises viscoelastic glycated chitosan; (b) introducing the chromophore and the immunoadjuvant into the neoplasm to obtain a conditioned neoplasm; and (c) irradiating the conditioned neoplasm whereby neoplastic cellular destruction of the conditioned neoplasm is induced producing fragmented neoplastic tissue and cellular molecules in the presence of the immunoadjuvant which stimulates the self-immunological defense system of the host against neoplastic cellular multiplication.

In yet another embodiment, a method of producing tumor specific antibodies in a tumor-bearing host, includes irradiating a tumor with a laser of a wavelength in the visible, near-infrared or infrared range, to a degree sufficient to induce neoplastic cellular destruction and generating fragmented neoplastic tissue and cellular molecules, followed by the introduction of an immunoadjuvant into or around a neoplasm by means of injection so that the host's immune system is stimulated to interact with and process fragmented neoplastic tissue and cellular molecules, upon which a systemic anti-tumor response is induced.

In another embodiment, a method of producing tumor specific antibodies in a tumor-bearing host, includes simultaneously introducing a chromophore and an immunoadjuvant into a neoplasm by intratumor injection to obtain a conditioned neoplasm, the chromophore being suitable to generate thermal energy upon activation in the near-infrared or infrared wavelength range; and activating the chromophore with a laser of a wavelength in the near-infrared or infrared range to a degree sufficient to activate the chromophore to produce a photothermal reaction inducing neoplastic cellular destruction and generating fragmented neoplastic tissue and cellular molecules.

An exemplary method of photophysically destroying a neoplasm and concurrently generating an in situ autologous vaccine in a tumor-bearing host, includes: (a) selecting an immunoadjuvant; (b) irradiating the neoplasm with a laser of a wavelength in the visible, near-infrared or infrared range, at a power and for a duration sufficient to produce a photothermal reaction inducing neoplastic cellular destruction and generating fragmented neoplastic tissue and cellular molecules; (c) forming the in situ vaccine by introducing the immunoadjuvant into the neoplasm by intratumor injection wherein the in situ vaccine comprises an amalgam of the fragmented tissue and cellular molecules and the immunoadjuvant; and (d) stimulating the self-immunological defense system against neoplastic cellular multiplication by having the vaccine presented locally to induce an anti-tumor response systemically within the host.

Another exemplary method of photophysically destroying a neoplasm and concurrently generating an in situ autologous vaccine in a tumor-bearing host, includes: (a) selecting a chromophore and an immunoadjuvant, the chromophore being suitable to generate thermal energy upon activation in the near-infrared or infrared wavelength range; (b) introducing the chromophore into the neoplasm by intratumor injection; (c) irradiating the neoplasm with a laser of a wavelength in the visible, near-infrared or infrared range, at a power and for a duration sufficient to activate the chromophore to produce a photothermal reaction inducing neoplastic cellular destruction and generating fragmented neoplastic tissue and cellular molecules; (d) forming the in situ vaccine by introducing the immunoadjuvant into the neoplasm by intratumor injection wherein the in situ vaccine comprising an amalgam of the fragmented tissue and cellular molecules and the immunoadjuvant; and (e) stimulating the self-immunological defense system against neoplastic cellular multiplication by having the vaccine presented locally to induce an anti-tumor response systemically within the host.

Yet another exemplary method of photophysically destroying a neoplasm and concurrently generating an in situ autologous vaccine in a tumor-bearing host, includes: (a) selecting a chromophore and an immunoadjuvant, the chromophore being suitable to generate thermal energy upon activation in the near-infrared or infrared wavelength range; (b) simultaneously or separately introducing the chromophore and the immunoadjuvant into the neoplasm by intratumor injection to obtain a conditioned neoplasm; (c) forming the in situ vaccine by irradiating the conditioned neoplasm with a laser of a wavelength in the near-infrared or infrared range at a power and for a duration sufficient to activate the chromophore to produce a photothermal reaction inducing neoplastic cellular destruction and generating fragmented neoplastic tissue and cellular molecules, wherein the in situ vaccine comprising an amalgam of the fragmented tissue and cellular molecules and the immunoadjuvant; and (d) stimulating the self-immunological defense system against neoplastic cellular multiplication by having the vaccine presented locally and by allowing the vaccine to be dispersed systemically within the host.

As described elsewhere herein, the method can further include conjugating the immunoadjuvant to a tumor specific antibody, thereby forming a conjugate, and administering the conjugate to the host. Alternatively, the method can further include conjugating the immunoadjuvant to a tumor specific antigen, thereby forming a conjugate, and administering the conjugate to the host. Any number of suitable chromophores can be used, for instance, indocyanine green, DHE, m-THPP, AlPcS$_4$, ZnET2, and Bchla.

Furthermore, the method can include conjugating a combination of the chromophore and the immunoadjuvant to a tumor specific antibody, thereby forming a conjugate, and administering the conjugate to the host. Alternatively, the method can further include conjugating the chromophore and the immunoadjuvant to a tumor specific antigen, thereby forming a conjugate, and administering the conjugate to the host. Any number of suitable chromophores can be used, for instance, indocyanine green, DHE, m-THPP, AlPcS$_4$. ZnET2, and Bchla.

The preparations and formulations of the present invention, including the viscoelastic glycated chitosan (GC) preparations, can also be used in conjunction with photodynamic therapy (PDT). Photosensitizing compounds show a photochemical reaction when exposed to light. Photodynamic therapy (PDT) uses such photosensitizing compounds and lasers to produce tumor necrosis. Treatment of solid tumors by PDT usually involves the systemic administration of tumor localizing photosensitizing compounds and their subsequent activation by laser. Upon absorbing light of the appropriate wavelength, the sensitizer is converted from a stable atomic structure to an excited state. Cytotoxicity and eventual tumor destruction are mediated by the interaction between the sensitizer and molecular oxygen within the treated tissue to generate cytotoxic singlet oxygen.

Two good general references pertaining to PDT, biomedical lasers and photosensitizing compounds, including light delivery and dosage parameters, are Photosensitizing Compounds: Their Chemistry, Biology and Clinical Use, published in 1989 by John Wiley and Sons Ltd., Chichester, U.K., ISBN 0 471 92308 7, and Photodynamic Therapy and Biomedical Lasers: Proceedings of the International Conference on Photodynamic Therapy and Medical Laser Applications, Milan, 24-27 Jun. 1992, published by Elsevier Science Publishers B.V., Amsterdam, The Netherlands, ISBN 0 444 81430 2, both incorporated herein by reference.

United States patents related to PDT include U.S. Pat. Nos. 5,095,030 and 5,283,225 to Levy et al.; U.S. Pat. No. 5,314,905 to Pandey et al.; U.S. Pat. No. 5,214,038 to Allison et al; and U.S. Pat. No. 5,258,453 to Kopecek et al., all of which are incorporated herein by reference. The Levy patents disclose the use of photosensitizers affected by a wavelength of between 670-780 nm conjugated to tumor specific antibodies, such as receptor-specific ligands, immunoglobulins or immunospecific portions of immunoglobulins. The Pandey patents are directed to pyropheophorbide compounds for use in standard photodynamic therapy. Pandey also discloses conjugating his compositions with ligands and antibodies. The Allison patent is similar to the Levy patents in that green porphyrins are conjugated to lipocomplexes to increase the specificity of the porphyrin compounds for the targeted tumor cells. The Kopecek patent also discloses compositions for treating cancerous tissues. These compositions consist of two drugs, an anti-cancer drug and a photoactivatable drug, attached to a copolymeric carrier. The compositions enter targeted cells by pinocytosis. The anti-cancer drug acts after the targeted cell has been invaded. After a period of time, a light source is used to activate the photosensitized substituent.

Further Application for Tumor Immunotherapy

The preparations and formulations of the present invention, including the viscoelastic glycated chitosan (GC) preparations, can be used, e.g., as immunoadjuvants, in the context of tumor immunotherapy.

The major functions of the immune system are to develop the concept of "self" and eliminate what is "nonself". Although microorganisms are the principal nonself entities encountered every day, the immune system also works to eliminate neoplasms and transplants.

There are several distinct types of immunity. Nonspecific, or innate, immunity refers to the inherent resistance manifested by a species that has not been immunized (sensitized or allergized) by previous infection or vaccination. Its major cellular component is the phagocytic system, whose function is to ingest and digest invading microorganisms. Phagocytes include neutrophils and monocytes in the blood and macrophages in the tissues. Complement proteins are the major soluble component of nonspecific immunity. Acute phase reactants and cytokines, such as interferon, are also part of innate immunity.

Specific immunity is an immune status in which there is an altered reactivity directed solely against the antigenic determinants (infectious agent or other) that stimulated it. It is sometimes referred to as acquired immunity. It may be active and specific, as a result of naturally acquired (apparent or unapparent) infection or intentional vaccination; or it may be passive, being acquired from a transfer of antibodies from another person or animal. Specific immunity has the hallmarks of learning, adaptability, and memory. The cellular component is the lymphocyte (e.g., T-cells, B-cells, natural killer (NK) cells), and immunoglobulins are the soluble component.

The action of T-cells and NK-cells in recognizing and destroying parasitized or foreign cells is termed cell-mediated Immunity. In contradistinction to cell-mediated immunity, humoral immunity is associated with circulating antibodies produced, after a complex recognition process, by B-cells.

As regards tumor immunology, the importance of lymphoid cells in tumor immunity has been repeatedly shown. A cell-mediated host response to tumors includes the concept of immunological surveillance, by which cellular mechanisms associated with cell-mediated immunity destroy newly transformed tumor cells after recognizing tumor-associated antigens (antigens associated with tumor cells that are not apparent on normal cells). This is analogous to the process of rejection of transplanted tissues from a nonidentical donor. In humans, the growth of tumor nodules has been inhibited in vivo by mixing suspensions of a patient's peripheral blood lymphocytes and of tumor cells, suggesting a cell-mediated reaction to the tumor. In vitro studies have shown that lymphoid cells from patients with certain neoplasms show cytotoxicity against corresponding human tumor cells in culture. These cytotoxic cells, which are generally T-cells, have been found with neuroblastoma, malignant melanomas, sarcomas, and carcinomas of the colon, breast, cervix, endometrium, ovary, testis, nasopharynx, and kidney. Macrophages may also be involved in the cell-mediated host's response to tumors when in the presence of tumor-associated antigens, lymphokines or interferon.

Humoral antibodies that react with tumor cells in vitro have been produced in response to a variety of animal tumors induced by chemical carcinogens or viruses. Hydridoma technology in vitro permits the detection and production of monoclonal antitumor antibodies directed against a variety of animal and human neoplasms. Antibody-mediated protection against tumor growth in vivo, however, has been demonstrable only in certain animal leukemias and lymphomas. By contrast, lymphoid cell-mediated protection in vivo occurs in a broad variety of animal tumor systems.

Immunotherapy for cancer is best thought of as part of a broader subject, namely biologic therapy, or the administration of biologic-response modifiers. These agents act through one or more of a variety of mechanisms (1) to stimulate the host's antitumor response by increasing the number of effector cells or producing one or more soluble mediators; (2) to serve as an effector or mediator; (3) to decrease host suppressor mechanisms; (4) to alter tumor cells to increase their immunogenicity or make them more likely to be damaged by immunological processes; or (5) to improve the host's tolerance to cytotoxics or radiation therapy. Heretofore the focus of cell-mediated tumor immunotherapy has been on reinfusion of the patient's lymphocytes after expansion in vitro by exposure to interleukin-2. One variation includes isolating and expanding populations of lymphocytes that have infiltrated tumors in vivo, so-called tumor-infiltrating lymphocytes. Another is the concurrent use of interferon, which is thought to enhance the expression of histocompatibility antigens and tumor-associated antigens on tumor cells, thereby augmenting the killing of tumor cells by the infused effector cells.

Humoral therapy has long concentrated on the use of antitumor antibodies as a form of passive immunotherapy, in contrast to active stimulation of the host's own immune system. Another variation is the conjugation of monoclonal antitumor antibodies with toxins, such as ricin or diphtheria, or with radioisotopes, so the antibodies will deliver these toxic agents specifically to the tumor cells. Active immunization with a host's own tumor cells, after irradiation, neuraminidase treatment, hapten conjugation, or hybridization has also been tried. Clinical improvement has been seen in a minority of patients so treated. Tumor cells from others have been used after their irradiation in conjunction with adjuvants in acute lymphoblastic leukemia and acute myeloblastic leukemia after remission. Prolongation of remissions or improved reinduction rates have been reported in some series, but not in most. Interferons, tumor necrosis factor and lymphotoxins have also been used to affect Immunologically mediated mechanisms. A recent approach, using both cellular and humoral mechanisms, is the development of "heterocross-linked antibodies," including one antibody reacting with the tumor cell linked to a second antibody reacting with a cytotoxic effector cell, making the latter more specifically targeted to the tumor. Host immune cell infiltration into a PDT treated murine tumor has been reported.

Combined PDT and Immunotherapy

In accordance with the present invention, it is desirable to utilize glycated chitosan (GC) preparations having a suitable viscosity that enables their use as an injectable material in additional applications, such as combined photodynamic cancer therapy (PDT) and tumor immunotherapy methods.

The potential for combining PDT with immunotherapy was explored by Korbelik, Krosl, Dougherty and Chaplin. See Photodynamic Therapy and Biomedical Lasers, supra, at pp. 518-520. In their study, they investigated a possibility of amplification of an immune reaction to PDT and its direction towards more pervasive destruction of treated tumors. The tumor, a squamous cell carcinoma SCCVII, was grown on female C3H mice. An immunoactivating agent SPG (a high molecular weight B-glucan that stimulates macrophages and lymphoid cells to become much more responsive to stimuli from cytokines and other immune signals) was administered intramuscularly in 7 daily doses either ending one day before PDT or commencing immediately after PDT. Photofrin based PDT was employed; photofrin having been administered intravenously 24 hours before the light treatment. The SPG immunotherapy was shown to enhance the direct killing effect of the PDT. The indirect killing effect (seen as a decrease in survival of tumor cells left in situ) was, however, much more pronounced in tumors of animal not receiving SPG. The difference in the effectiveness of SPG immunotherapy when performed before and after PDT suggested that maximal interaction is achieved when immune activation peaks at the time of the light delivery or immediately thereafter. With SPG starting after PDT (and attaining an optimal immune activation 5-7 days later), it is evidently too late for a beneficial reaction.

In another study the use of PDT to potentiate the effect of bioreactive drugs that are cytotoxic under hypoxic conditions was investigated. See Photodynamic Therapy and Biomedical Lasers, supra, at pp. 698-701. It was found that the antitumor activity of such drugs could be enhanced in vivo when they were used in combination with treatments that increase tumor hypoxia.

Cancer Treatment by Photodynamic Therapy, in Combination with an Immunoadjuvant

In accordance with the present invention, it is desirable to utilize glycated chitosan (GC) preparations having a suitable viscosity as injectable materials for use in the treatment of cancer. This can be achieved in any suitable manner, for instance, in conjunction with applications such as combined photothermal or photodynamic cancer therapy (PDT) and tumor immunotherapy methods. The term cancer, as used herein, is a general term that is intended to include any of a number of various types of malignant neoplasms, most of which invade surrounding tissues, may metastasize to several sites, and are likely to recur after attempted removal and to cause death of the patient unless adequately treated. A neoplasm, as used herein, refers to an abnormal tissue that grows by cellular proliferation more rapidly than normal. It continues to grow even after the stimulus that initiated its growth dissipates. Neoplasms show a partial or complete lack of structural organization and functional coordination with the normal tissue and usually form a distinct mass which may be either benign or malignant.

In accordance with the present invention, certain examples of cancers that may be treated with glycated chitosan (GC) preparations having a suitable viscosity as injectable materials include, but are not limited to, those of the cervix, breast, bladder, colon, prostate, larynx, endometrium, ovary, oral cavity, kidney, testis (nonsemino-matous) and lung (non-small cell).

Moreover, in accordance with the present invention, treatment may also be administered in a suitable manner in conjunction with other types of cancer treatment, for instance, radiation treatment. Radiation plays a key role, for example, in the remediation of Hodgkin's disease, nodular and diffuse non-Hodgkin's lymphomas, squamous call carcinoma of the head and neck, mediastinal germ-cell tumors, seminoma, prostate cancer, early stage breast cancer, early stage non-small cell lung cancer, and medulloblastoma. Radiation can also be used as palliative therapy in prostate cancer and breast cancer when bone metastases are present, in multiple myeloma, advanced stage lung and esophagopharyngeal cancer, gastric cancer, and sarcomas, and in brain metastases. Cancers that may be treated include, for instance, Hodgkin's disease, early-stage non-Hodgkin's lymphomas, cancers of the testis (seminormal), prostate, larynx, cervix, and, to a lesser extent, cancers of the nasopharynx, nasal sinuses, breast, esophagus, and lung.

Treatment may also be administered in a suitable manner in conjunction with other types of antineoplastic drugs. Antineoplastic drugs include those that prevent cell division (mitosis), development, maturation, or spread of neoplastic cells. The ideal antineoplastic drug would destroy cancer cells without adverse effects or toxicities on normal cells, but no such drug exists. Despite the narrow therapeutic index of many drugs, however, treatment and even cure are possible in some patients. Certain stages of choriocarcinoma, Hodgkin's disease, diffuse large cell lymphoma, Burkitt's lymphoma and leukemia have been found to be susceptible to antineoplastics, as have been cancers of the testis (nonseminomatous) and lung (small cell). Common classes of antineoplastic drugs include, but are not limited to, alkylating agents, antimetabolites, plant alkaloids, antibiotics, nitrosoureas, inorganic ions, enzymes, and hormones.

In Situ Autologous Cancer Vaccines, Such as Laser-Assisted Immunotherapy

The chitosan-derived compositions and, in particular, the viscoelastic glycated chitosan preparations of the present invention, are effective in treating neoplasms and other medical disorders. Additional uses of glycated chitosan, alone or in combination with other drugs, include use as an immunostimulant in the treatment of immuno-compromised patients including but not limited to cancer and acquired immunodeficiency syndrome.

The chitosan-derived compositions of the present invention are thus useful in a myriad of applications, including for instance as an immunoadjuvant or as a component of an immunoadjuvant, as described in detail herein. Notwithstanding other uses, a principal use of the chitosan-derived compositions is as an immunoadjuvant in connection with in situ autologous cancer vaccines (inCVAX), such as laser-assisted immunotherapy (LIT), and it is in this context that the chitosan-derived compositions are described in detail herein.

As described further herein, additional embodiments of the present invention are directed to uses of the glycated chitosan preparations of the present invention as immunoadjuvants in conjunction with inCVAX in general, and LIT in particular, for cancer treatment. Laser-assisted immunotherapy utilizing the present invention preferably encompasses introducing into or around a neoplasm an immunoadjuvant comprising viscoelastic chitosan-derived compositions following photothermal irradiation of the same tumor. The photothermal action is performed at an irradiance sufficient to induce neoplastic cellular destruction, which can be performed with or without intratumoral injection of, or by other means delivered, a chromophore, and combined with injection of, or by other means delivered, the viscoelastic glycated chitosan preparations of the present invention, cell-mediated and humoral anti-tumor immune responses are induced.

In preferred embodiments, improved LIT is provided wherein the improvement comprises the use of the herein-described injectable viscoelastic glycated chitosan preparations of the present invention. The present invention also contemplates methods of in vivo activation of specific components of the immune system in conjunction with inCVAX in general, or LIT in particular, comprising treatment with a viscoelastic glycated chitosan preparation.

As described further herein, it has been determined that LIT provides an in situ autologous cancer vaccine (inCVAX) that overcomes limitations of current immunotherapies and cancer vaccines. In general, the two principles underlying LIT are (1) local heating of the primary tumor with a laser to devitalize the tumor and liberate tumor antigens, and (2) local injection of a potent and nontoxic immunoadjuvant comprising glycated chitosan (GC), which interacts with liberated tumor antigens to induce an immune response against the cancer. Thus, LIT effectively functions as an in situ autologous cancer vaccine that uses whole tumor cells as the sources of tumor antigens from each individual patient without pre-selection of tumor antigens or ex vivo preparation.

In accordance with the present invention, another advantage of using the herein-described injectable viscoelastic glycated chitosan preparations of the present invention, in conjunction with LIT, is that by using this LIT approach, there is activation of dendritic cells (DC), and subsequently exposure of the activated DC to tumor antigens in vivo. LIT thus represents an advantageous approach to other whole-cell cancer vaccinations, by eliminating the need of ex vivo preparations, and by using LIT in conjunction with the viscoelastic glycated chitosan preparations as immunoadjuvants.

One exemplary formulation of a glycated chitosan preparation was manufactured under the name PROTECTIN. It has been observed that PROTECTIN in conjunction with LIT stimulates the immune system and induces tumor-specific immunity by 1) activating dendritic cells, 2) increasing the interaction between tumor cells and dendritic cells, and 3) increasing the tumor antigen presentation to the immune system.

Other viscoelastic glycated chitosan preparations of the present invention also function to stimulate the immune system and induce tumor-specific immunity by 1) activating dendritic cells, 2) increasing the interaction between tumor cells and dendritic cells, and 3) increasing the tumor antigen presentation to the immune system.

Thus, in accordance with a preferred embodiment of the invention, formulations of viscoelastic glycated chitosan activate one or more components of the immune system, mediating desired therapeutic effects.

As described further herein, certain components of the immune system that are activated include components of nonspecific, or innate, immunity, namely the phagocytic system including neutrophils and monocytes in the blood and macrophages in the tissues; complement proteins, the major soluble component of nonspecific immunity; and acute phase reactants and cytokines, such as interferon, also part of innate immunity. There are many different components of specific immunity, for example, the lymphocyte (e.g., T-cells, B-cells, natural killer (NK) cells), and immunoglobulins. The glycated chitosan formulations of the invention also interact with lymphoid cells to promote tumor immunity. Macrophages may also be involved in the cell-mediated hosts response to tumors when in the presence of tumor-associated antigens, lymphokines or interferon.

Specific components of the immune system are activated after "photothermal" treatment. When photothermal destruction occurs, the fragmented tissue and cellular molecules are disbursed within the host in the presence of the immunologically potentiating material, such as chitosan. In effect, an in situ vaccine is formed. This mixture of materials then circulates in the host and is detected by the immunological surveillance system. There follows an immediate mobilization of cell-mediated immunity which encompasses NK-cells and recruited killer T-cells. These cells migrate to the sites of similar antigens or chemicals. In time, the cell-mediated immunity shifts to a humoral immunity with the production of cytotoxic antibodies. These antibodies freely circulate about the body and attach to cells and materials for which they have been encoded. If this attachment occurs in the presence of complement factors, the result is cellular death.

The injectable viscoelastic glycated chitosan preparations of the present invention have unexpected utility in "in situ cancer vaccines", which are based on an in situ activation of antigen-presenting cells (e.g., dendritic cells and macrophages), and the subsequent exposure of tumor antigens to the antigen-presenting cells. The injectable viscoelastic glycated chitosan preparations of the present invention also activate other cellular mediators including, but not limited to, tumor necrosis factor (e.g., TNFa) and nitric oxide which contribute to the therapeutic effects.

Another advantage of using the herein-described injectable viscoelastic glycated chitosan preparations of the present invention, in conjunction with LIT, is that by using this approach, this method independently triggers the immune response in each individual, and it does not depend upon cross reactivity in the expression of tumor-specific antigen between hosts (as is required in conventional antibody immunotherapy and vaccination). Histochemical studies have revealed that sera from LIT-cured tumor-bearing rats contained antibodies that bound to the plasma membrane of both living and preserved tumor cells. Western blot analysis of tumor cell proteins using sera (from rats successfully treated by LIT) as the source of primary antibodies showed distinct bands, indicating induction of tumor-selective antibodies. It was also shown that successfully treated rats could acquire long-term resistance to tumor re-challenge, and adoptive immunity could be transferred using spleen cells from successfully treated rats, indicating tumor-specific immunity.

Thus, using the herein-described injectable viscoelastic glycated chitosan preparations of the present invention, there are several advantages that meet critical needs in providing effective cancer treatment. This is particularly advantageous for cancer patients, since the present invention also provides surprisingly and unexpectedly beneficial preparations that are easy to administer by injection, and therefore increase compliance and provide effective treatment alternatives to conventional approaches that do not provide (1) effective, (2) nontoxic, and (3) practical treatments for late-stage metastatic cancer. A critical issue in breast cancer therapy is that not all patients are treatable with current, conventional methodologies and those diagnosed at late stages have a poor prognosis, with even fewer valid options for treatment. And, while there have been many advances and developments in breast cancer treatment in recent years, crucial problems remain. The injectable viscoelastic glycated chitosan preparations of the present invention, as described herein, provide several advantages that meet critical needs in providing effective cancer treatment.

LIT has been shown to induce maturation of dendritic cells (assessed by CD80 expression), enhance T-cell proliferation, increase IFN-γ secretion and increase HSP70 expression. Furthermore, the combined effects of LIT (for instance, tumor heating with a laser and injection of glycated chitosan preparations in accordance with the present invention) has been shown to induce tumor-specific immunity, with an infiltration of tumor-specific cytotoxic CD4 and CD8 cells into the tumors following the treatment.

As described in further detail herein, LIT thus provides numerous advantages including, but not limited to:

Eliminates treated primary tumors
Eliminates untreated metastases
Induces long-term immunity and survival
Creates resistance to tumor rechallenges
Is non-toxic and safe to use in humans at therapeutic doses In accordance with one aspect of the invention, a neoplasm, such as a malignant tumor, is irradiated with visible, near-infrared or infrared light with a power and a duration sufficient to elevate the temperature of the neoplasm to a level that induces neoplastic cellular destruction and stimulates the self-immunological defense system against neoplastic cellular multiplication. To facilitate the heating of the tumor, a chromophore with absorption peaks corresponding to the wavelength of the applied light, may be injected prior to applying the light treatment. Following the light irradiation, a viscoelastic glycated chitosan-derived immunoadjuvant is administered, for example by injection, into the tumor or the tissue immediately surrounding the tumor.

In accordance with another aspect of the invention, a solution of indocyanine green (ICG) and glycated chitosan is prepared at a concentration of 0.1 to 2% of ICG to chitosan. The solution is injected into the neoplasm, and the neoplasm is then irradiated using a laser having a power of about 5 watts and a wavelength of radiation capable of readily penetrating normal cellular tissues without significant disruption. The irradiation continues for a duration of from about one to about ten minutes, which is sufficient to elevate the temperature of the neoplasm to a level that induces neoplastic cellular destruction and stimulates cell-mediated and humoral immune responses.

As described further herein, the present invention has several advantages over other conventional and unconventional treatment modalities. The combination of tumor destruction and immune-stimulation adjuvant is the key. The most significant advantage is combined acute and chronic tumor destruction. The acute tumor loss is caused by photovaporization, photoablation or thermal killing of the neoplastic tissue, on a large and controlled scale, in the immediate area, reducing the tumor burden and hence the base of multiplication so that the self-defense system can fight a weaker "enemy". When local tumor destruction occurs, the fragmented tissue and cellular molecules are locally disbursed within the host in the presence of the immunologically potentiating material, such as glycated chitosan. In effect, an in situ vaccine is formed. There follows an immediate mobilization of cell-mediated immunity which encompasses NK-cells and recruited killer T-cells. These cells migrate to the sites of similar antigens or chemicals. In time, the cell-mediated immunity shifts to a humoral immunity with the production of cytotoxic antibodies. These antibodies freely circulate about the body and attach to cells and materials for which they have been encoded. If this attachment occurs in the presence of complement factors, the result is cellular death. The time frames for these two immunological modes of action are 0 to 2 weeks for the cell-mediated response, while the humoral arm matures at approximately 30 days and should persist for long periods, up to the life span of the host.

In summary, long-term survival with total cancer eradication can be achieved by using the viscoelastic glycated chitosan preparations of the present invention. It is a combined result of reduced tumor burden due to ablative (for example photothermal) interactions and an enhanced immune system response due to the presence of glycated chitosan or other immunomodulators.

According to other embodiments, the glycated chitosan preparations of the present invention may also be used for antimicrobial and/or hemostatic applications. Thus the glycated chitosan (GC) preparations can be formulated, for instance, as an antimicrobial hemostatic spray, wherein the GC formulation has a viscosity and exhibits rheological properties that enable it to be sprayed from conventional containers. Moreover, GC can be included in other formulations provided that it is applied in antimicrobial and/or hemostatic effective concentrations and with viscosities/rheological properties that enable its ability to be dispensed from containers suitable for the purpose.

The present invention is further illustrated by the following examples. These examples are provided by way of illustration and are not intended in any way to limit the scope of the invention. The examples should therefore not be construed as limitations on the scope of the invention, but rather should be viewed as exemplifications of preferred embodiments thereof. Many other variations are possible.

EXAMPLES

Example 1

Exemplary Process for the Preparation of Glycated Chitosan (GC)

Glycated chitosan is obtained by reacting chitosan with a monosaccharide and/or oligosaccharide, preferably in the presence of an acidifying agent, for a time sufficient to accomplish Schiff base formation between the carbonyl group of the sugar and the primary amino groups of chitosan (also referred to herein as glycation of the amino group) to a predetermined degree whereby a predetermined percent (%) glycation of the chitosan polymer is achieved. This is followed by stabilization by reduction of Schiff bases and of their rearranged derivatives (Amadori products). NMR tracings are used to verify the bonding of the monosaccharides and/or oligosaccharides to the chitosan polymer, whereas chemical measurement of remaining free amino groups, such as via a ninhydrine reaction, is used to assess the degree of glycation.

Example 2

Sterile Filtration

While conventional 1500 kDa galactochitosan, described in U.S. Pat. No. 5,747,475, is relatively simple to synthesize, the sterilization with, for example a 0.22 micron filter, is impossible without compromising the integrity of the filter, thus rendering the conventional glycated chitosan unsuitable for GMP production and human use. In contrast, the new viscoelastic glycated chitosan described herein has significant advantages with regard to GMP production and sterile filtration due to unexpected and beneficial physiochemical properties. For example, at a molecular weight (M.W.) of 250,000 Da (250 kDa), sterile filtration with a 0.22 micron filter is highly feasible, with a flow rate of 100 ml/min without loss of material during filtration.

Example 3

Viscosity of Glycated Chitosan (GC)

GC preparations of higher molecular weight display higher viscosities (measured in Cp):

| kDa of GC | Cp |
| --- | --- |
| 100 | 0.914 |
| 250 | 7.68 |
| 500 | 20.79 |
| 1500 | 84.7 |

Figure 3:
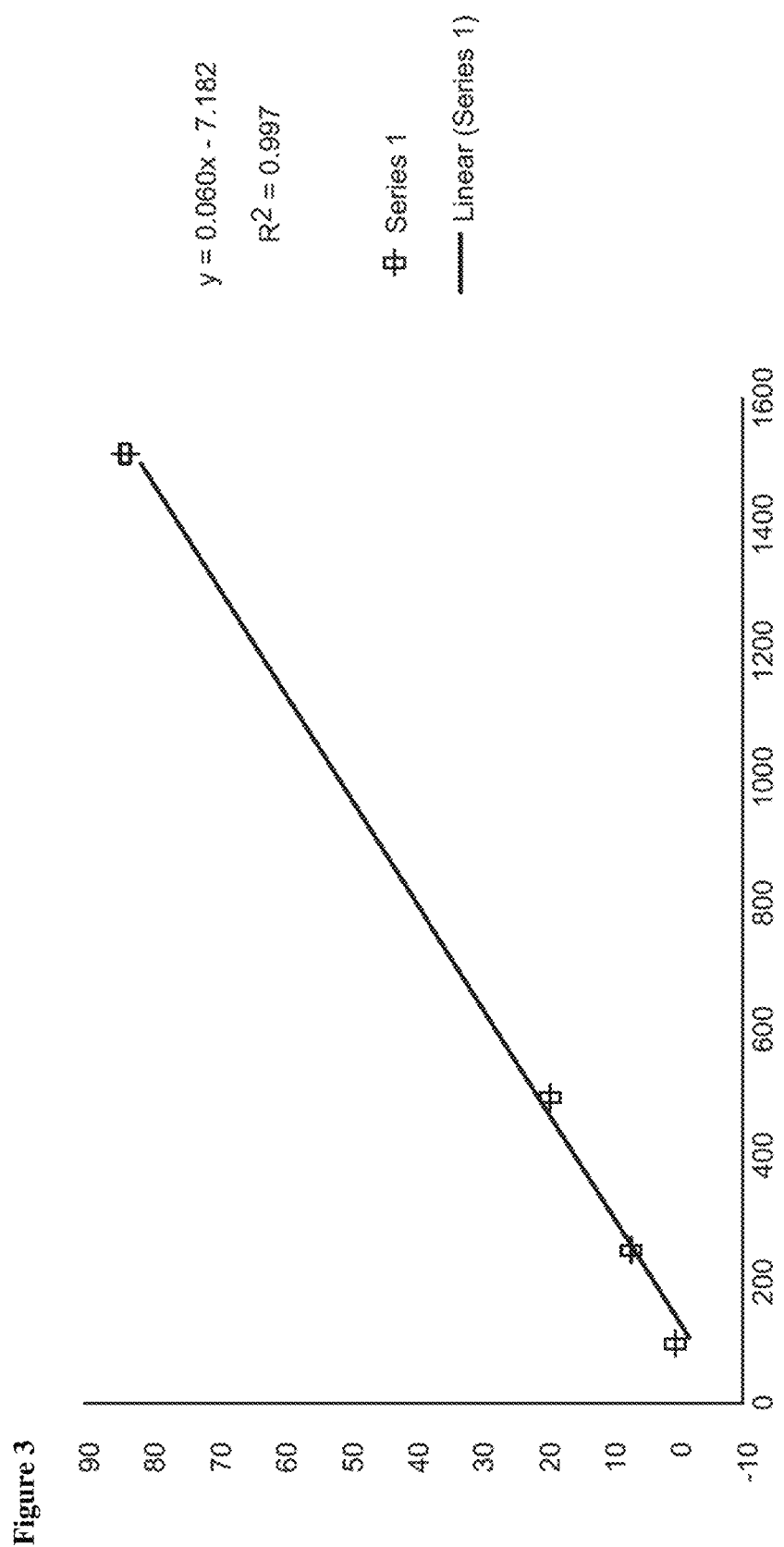
FIG. 3 depicts a graph that shows viscosity (in Cp: y-axis) vs. molecular weight (in kDa; x-axis) in samples of GC with molecular weights ranging from 100 kDa to 1,500 kDa).

FIG. 3 shows viscosity (in Cp; y-axis) vs. molecular weight (in kDa; x-axis) in samples of GC with molecular weights ranging from 100 kDa to 1,500 kDa. The concentration of GC in solution in this experiment decreased with increasing molecular weight, ranging from 0.6% (100 kDa) to 0.11% (1,500 kDa).

Figure 4:
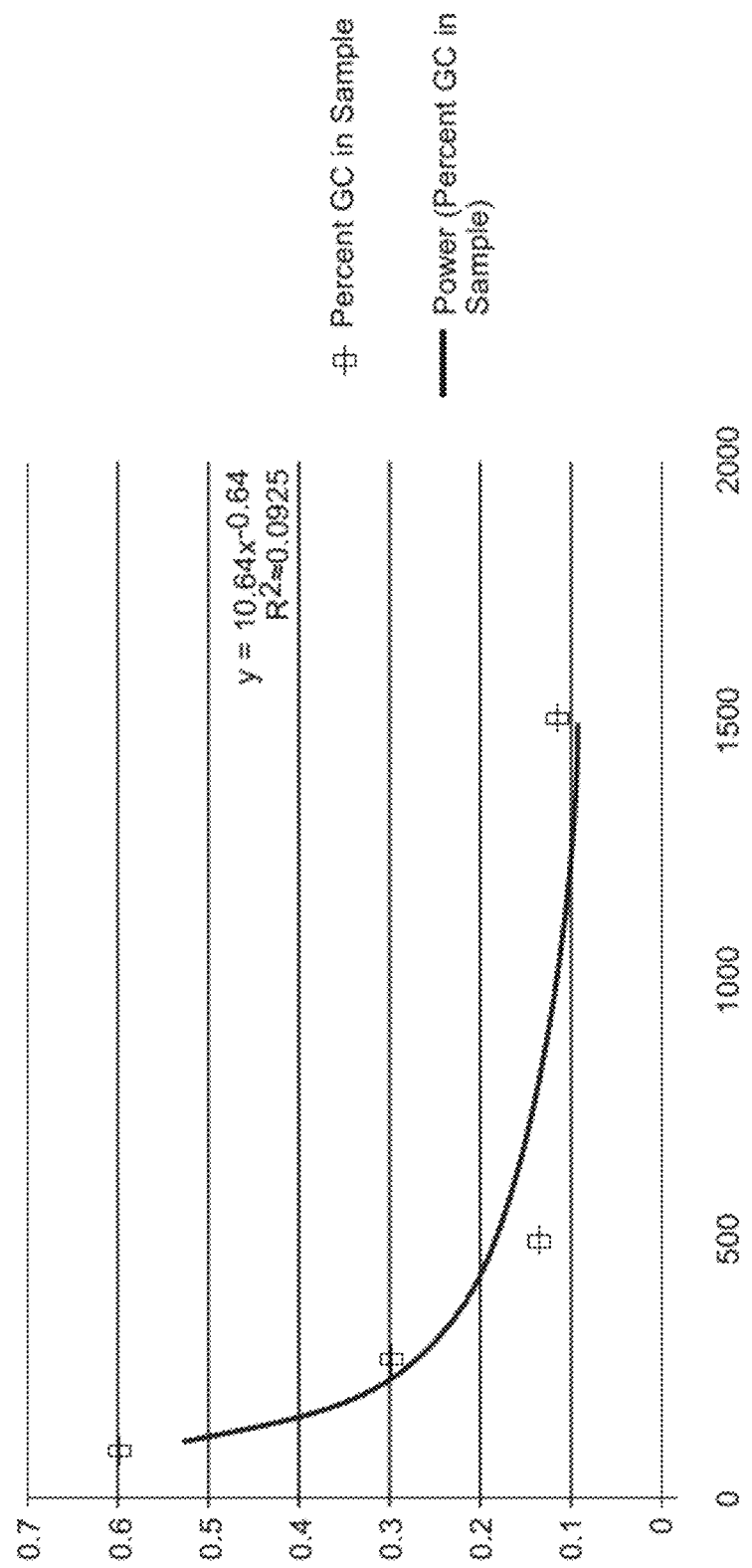
FIG. 4 depicts a graph that shows the percent of GC in solution of the samples used in the viscosity experiment.

Very surprisingly, it was found viscosity increases linearly with increasing molecular weight only if the concentration of GC in the sample is reduced with increasing molecular weight. The table and FIG. 4 shows the percent of GC in solution of the samples used in the viscosity experiment above.

| Size kDa | Percent GC in Sample |
| --- | --- |
| 100 | 0.6 |
| 250 | 0.3 |
| 500 | 0.14 |
| 1500 | 0.11 |

The results clearly show that 1) GC preparations of higher molecular weight correlate with higher viscosities (measured in Cp), and 2) the correlation between viscosity and molecular weight is not linear if the concentration is kept constant. In other words, the viscosity increases disproportionally with increasing molecular weight, which renders the higher molecular weight glycated chitosans (such as those disclosed in U.S. Pat. No. 5,747,475) unsuitable for injection or sterile filtration.

Viscoelastic glycated chitosan preparations comprising lower molecular weight (i.e. below ~400 kDa) glycated chitosan thus provide improved injectability; these preparations are useful, for instance, for cancer treatments utilizing photodynamic therapy and laser-assisted immunotherapy to induce neoplastic cellular destruction and to stimulate the self-immunological defense system against neoplastic cells.

Example 4

Improvement of Manufacturing

In this exemplary study, it was determined that experimental conditions could be adjusted as needed to improve overall yield during the manufacture of glycated chitosan. It was unexpectedly discovered that manufacturing of GOC could be improved by controlling the pH conditions, and thus controlling the percent glycation. Specifically, it was determined that because the half-life of sodium borohydride ($NaBH_4$) is proportional to pH, meaning that at lower pH the half-life of $NaBH_4$ is extremely short, and only at higher pH is the $NaBH_4$ somewhat more stable. It was thus determined that $NaBH_4$ was not as effective in stabilizing the glycated chitosan by reduction of the Schiff bases and Amidori products at lower pH. For instance, when the pH was kept below five (pH<5), the half-life of NaBH4 is extremely short, and thus the reduction of the Schiff bases and Amadori products was less efficient, and percent glycation of GC thus went down.

It was determined, however, that with a higher pH, the formulation "gels" and becomes non-newtonian. For instance, when the pH was kept above six (pH>6), the formulation was observed to gel and thus the batch had to be discarded. In other words, to achieve the goal of efficient GC manufacturing, the pH was not kept so high that the formulation would "gel", but the pH was also not kept so low that the percent glycation was minimized due to the short half life of $NaBH_4$.

Example 5

Laser-Assisted Immunotherapy (UT) Treatment in a Human Trial

An investigator-driven breast cancer trial was performed on 10 patients with advanced breast cancer (5 stage IV, 5 stage III). Most of the patients had responded poorly, or not at all, to conventional modalities, and received at least one Laser-Assisted Immunotherapy (LIT) treatment in which viscoelastic glycated chitosan was used as the immunoadjuvant. Two (2) patients withdrew prematurely due to unrelated reasons, leaving 8 evaluable patients. The independent investigators acquired IRB and government approvals prior to the trials. Biopsies and medical imaging (CT scans, etc.) were used for the evaluation of the primary lesions and metastasis.

The primary efficacy parameter was the best overall response by the investigators' assessments using Response Evaluation Criteria in Solid Tumors (RECIST). Complete response (CR) was defined as disappearance or lack of qualifying metabolic activity of all target lesions. Partial response (PR) was defined as a ≥30% decrease from baseline in activity or in the sum of the longest diameter of target lesions. Progressive disease (PD) is defined as a ≥20% increase in the sum of the longest diameter of target lesions or the appearance of 1 or more new lesions. Stable disease (SD) was defined as neither sufficient reduction to qualify for PR nor sufficient increase to qualify for PD.

Of the 8 breast cancer patients available for evaluation, CR was observed in 1 patient, PR in 4 patients and SD in 1 patient. In patients available for evaluation, the objective response rate (CR+PR) was 62.5%, and the clinically beneficial response rate (CR+PR+SD) was 75%. PD was observed in 2 patients. All local lesions irradiated by laser responded to LIT. In addition, most of the distant metastases of these patients responded to LIT. The diameters and activity of the metastases in lymph node, lung and liver in several patients decreased dramatically.

Local and systemic toxicity was graded according to National Cancer Institute Common Toxicity Criteria, version 3.0. Laboratory assessment and physical examinations were performed periodically. Adverse events were closely monitored and recorded throughout the study period. LIT only induced local reactions within the treatment area in breast cancer patients, most of which were related to the thermal effects of the topical laser treatment. Redness, pain, edema and ulceration of the treatment area were the common adverse events (AEs). No grade 3 or 4 adverse events were observed. In patients who had not received prior radiation therapy the swelling was minor. For the patients who have received prior radiation therapy, the swelling was more substantial with longer duration.

Example 6

Laser-Assisted Immunotherapy with Glycated Chitosan Demonstrates Antitumor Immunity Against 816 Melanoma Tumors in Mice Female C57BC/6 mice (8 weeks of age; 12 mice/group) were subcutaneously inoculated with the B16-F1 melanoma tumor ($10^6$ viable tumor cells) into the back area. The tumors reached treatment size (7 to 8 mm in diameter) around 7 days after implantation. Five treatment groups (12 female mice/group) were included in the study: an untreated control; laser-assisted immunotherapy treatment control; and laser-assisted immunotherapy treatment with 0.2 mL of 1% glycated chitosan peritumorally injected 24 h prior, immediately following, or 24 h after laser treatment. The 805 nm diode laser was used for laser irradiation, with parameter settings of 2 W for 10 min in duration. The laser was directed through an optical fiber with a diffuser lens at the end to the treatment site and the laser tip was maintained at a distance of 4 mm from the skin.

Animal survival was evaluated. Darkening and hardening of the mouse skin at the treatment site was observed after laser treatment. Tumor reoccurrence usually occurred several days after treatment. Thermal treatment in combination with glycated chitosan application resulted in a significant improvement in animal survival with glycated chitosan administered 24 h before laser irradiation showing the most significant improvements (see table below).

Effect of laser and Glycated Chitosan Treatment in B16 Melanoma Tumor-Bearing Mice[n]

| Treatment Injection* | Long-Term (>90 Days) Survival Rate (%)[b] |
|---|---|
| Untreated Control | 0.0 |
| Laser Only | 16.7 |
| Laser + 0.2 mL 1% GC 24 h After Laser | 16.7 |
| Laser + 0.2 mL 1% GC 24 h Immediately After Laser | 25.05 |
| Laser + 0.2 mL 1% GC 24 h Before Laser | 41.7 |

* = 805 nm diode laser with energy (2W, 10 min.) directed through an optical fiber with a diffuser lens that was maintained at a distance of 4 mm from the skin
[b] = Long-term survival was defined as >90 days after inoculation without tumor recurrence
GC = Glycated chitosan
[n] = 12 female C57BC/6 mice Example 7

Figure 5:
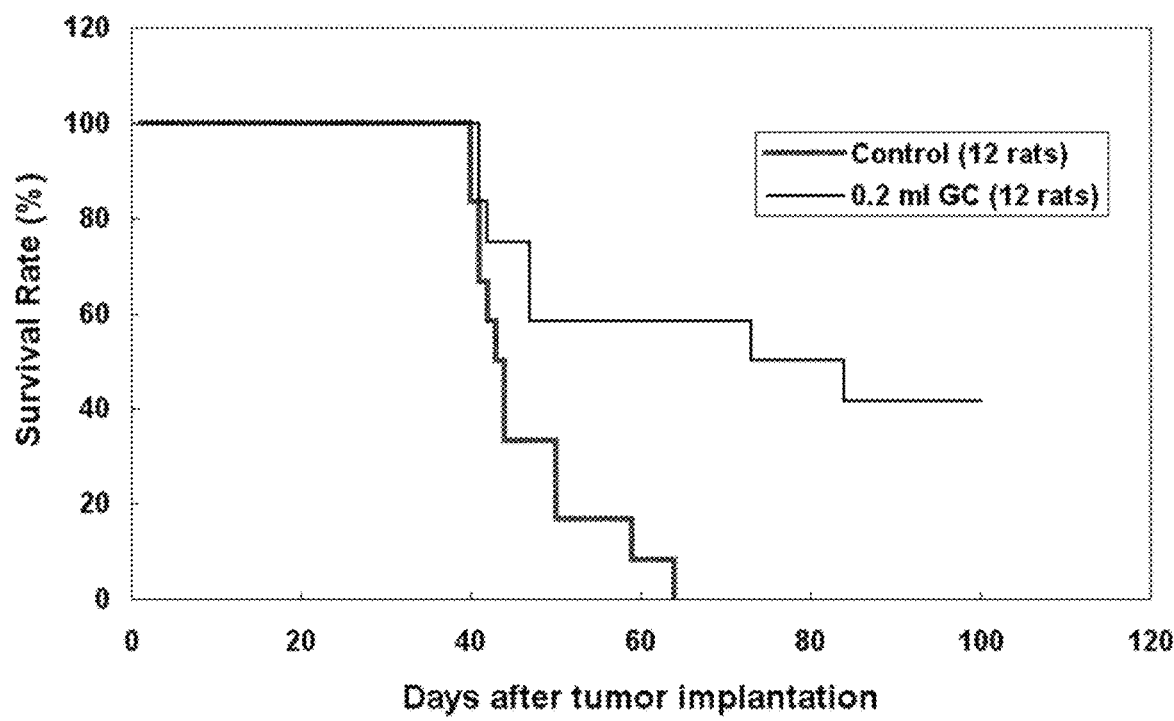
FIG. 5 depicts a graph that shows the survival rates following interstitial laser-assisted immunotherapy with 0.2 ml of GC.

Interstitial Laser-Assisted Immunotherapy in a Metastatic Mammary Model Using 805 nm Laser and Glycated Chitosan A study was conducted to determine the optimal interstitial laser dose and the optimal glycated chitosan dose. Female Wistar Furth rats (5 to 6 weeks of age, 100 to 125 g) were subcutaneously injected with the transplantable, metastatic mammary tumor, DMBA-4, ($10^5$ viable tumor cells) into the back area. DMBA-4 tumors, originally induced chemically, are highly metastatic and poorly immunogenic. The tumors metastasize along the lymphatics and rapidly form multiple metastases at distant sites, killing all the rats 30 to 40 days after tumor implantation. When the primary tumor was 0.2 to 0.5 $cm^3$, the hair overlying the tumor was dipped and laser-assisted immunotherapy was performed on anesthetized animals (2% isofluorane). An 805 nm diode laser was used to deliver near-infrared light for target tumors. Continuous laser power was delivered through an optical fiber with an active cylindrical tip. An active tip of 1.0 cm was used, with a transparent plastic sheath to protect the active tip. For the insertion of the active fiber tip, either needle-guided or puncture-assisted insertion methods were used. The intratumoral position of the fiber was verified by a digital camera, which can capture the infrared light from the 805-nm laser. The rats were observed daily and the tumors were measured twice a week for a period of at least 100 days. The criterion for successful treatment was a 100-day survival after tumor implantation. The optimal interstitial laser dose was determined by evaluating effects in a control (9 rats, no treatment); interstitial laser powers of 1, 1.5, 2, 2.5, and 3 W/$cm^2$ for 10 min (14 rats/group); and interstitial laser power of 2 W/$cm^2$ for 30 min (14 rats/group). The rats in the 3 W at 10 min and 2 W at 30 min appeared to have average survival rates higher than other groups. The optimal glycated chitosan dose was determined by evaluating survival following administration of 0.1, 0.2, 0.4, and 0.6 mL of 1% glycated chitosan following interstitial laser-assisted immunotherapy at 2.5 W for 20 min. A group of rats that received no treatment was included as a control. The best survival, at 42%, was observed following a 0.2 mL glycated chitosan dose (see FIG. 5).

Example 8

Induced Antitumor Immunity Against DMBA-4 Metastatic Mammary Tumors in Rats Using Laser-Assisted Immunotherapy Female Wistar Furth rats (6 to 7 weeks of age, 110 to 130 g) were inoculated with the DMBA-4 transplantable, metastatic mammary tumor ($10^5$ viable tumor cells) into the inguinal area. The primary tumor generally appeared 7 to 10 days after inoculation and was approximately 1 to 5 g within 3 weeks. The tumor metastasized through the lymphatics to inguinal and axillary lymph nodes. Treatment was initiated when the primary tumor was 0.2 to 0.5 $cm^3$, generally 10 to 15 days after inoculation. Rats were administered a 0.25% indocyanine green and 1% Glycated Chitosan Solution (0.20 ml) injected directly into the center of the tumor prior to irradiation. An 805 nm diode laser was used for laser irradiation, with parameter settings of 2 W for 10 min in duration. The laser was directed through an optical fiber to the treatment site. Following irradiation, animals were housed individually and observations and tumor measurements were recorded twice weekly. Rats which were successfully treated (cured rats) were rechallenged repeatedly with the same tumor cells at tumor dose levels of $10^5$ to $10^7$ viable tumor cells per rat and animals were observed for 4 months for tumor development. Of the 32 rats treated by laser-assisted immunotherapy, eight rats were successfully treated and tumor-free for >120 days following inoculation. In all cured rats, metastases continued to develop after treatment, then gradually declined and eventually disappeared without additional treatment. Seven successfully-treated rats were rechallenged up to three times with dose levels ranging from $10^5$ to $10^7$ viable tumor cells per injection. There was no primary or metastatic tumor reemergence in any of these animals and animals survived >120 days, while untreated control rats developed primary and metastatic tumors and had an average survival of 30 days.

Example 9

Enhancement of Laser Cancer Treatment by a Chitosan-Derived Immunoadjuvant

The effect of the immunoadjuvant during the laser-assisted immunotherapy treatment was evaluated in rats using four different immunoadjuvants. Female Wistar Furth rats (6 to 8 weeks of age, 150 to 200 g) were subcutaneously inoculated with the DMBA-4 transplantable, metastatic mammary tumor ($10^5$ viable tumor cells) in the inguinal fat pad, 7 to 10 days before treatment. The primary tumor generally became palpable in 5 to 7 days and the remote inguinal and axillary metastases appeared 15 to 20 days after inoculation. The laser-assisted immunotherapy treatment was initiated when the primary tumor reached 0.2 to 0.5 cm$^3$. Laser treatment was generally performed on Day 10. The immunoadjuvants included aqueous 1% Glycated Chitosan Solution (0.2 mL dose; n=48 rats in two experiments), 50% Complete Freund's Adjuvant (0.2 mL dose; n=33 rats), 50% Incomplete Freund's Adjuvant (0.2 mL dose; n=30 rats), and *Corynebacterium parvum* (*C. parvum*; 35 µg/rat dose; n=32 rats). The immunoadjuvants were mixed with 0.25% indocyanine green and injected directly into the center of the tumor 2 h before irradiation with the 805 nm diode laser. Animals were anesthetized prior to irradiation and the hair overlying the primary tumor was dipped. The laser parameters were 2 W for 10 min with a 3 mm diameter laser treatment site, resulting in a fluence of 96 J/cm$^2$ for a 1 cm diameter tumor. Animals were individually housed, observed daily, and tumor burden measurements were collected twice a week.

3 Data from this study was compared with data from tumor-bearing control rats (n=38 rats) in several different experiments. All immunoadjuvants had a statistically significant increase in survival rate compared to control data (p<0.05). The 1% glycated chitosan appeared to be the most effective immunoadjuvant with a 29% long-term survival rate (see table below). Statistical significance was observed when the glycated chitosan adjuvant was compared to the *C. parvum* (p=0.009) and Incomplete Freund's Adjuvant (p=0.03). Although not significant, a noticeable improvement in survival was observed when compared to Complete Freund's Adjuvant that had a comparable cure rate (18%). A relative weak survival rate was observed following treatment with the Incomplete Freund's Adjuvant and *C. parvum*.

Long-term Survival Rates Following treatment with Four Different Immunoadjuvants

| Treatment | Number of Rats | Long-Term Survival Rate (%) |
|---|---|---|
| Control | 38[a] | 0 |
| Laser + ICG + Glycated Chitosan | 48[b] | 29 |
| Laser + ICG + Complete Freund's Adjuvant | 33 | 18 |
| Laser + ICG + Incomplete Freund's Adjuvant | 30 | 7 |
| Laser + ICG + *C. parvum* | 32 | 9 |

[a] = Tumor-bearing control rat data was collected from several control groups in different studies
[b] = Data collecte from two separate experiments
ICG = Indocyanine green Example 10

Enhancement of Photodynamic Therapy by a Chitosan-Derived Immunoadjuvant

To evaluate photodynamic therapy as a the method for direct tumor destruction in combination with glycated chitosan, a combination of photofrin- and meso-substituted tetra (meta-hydroxy-phenyl) chlorin-(mTHPC) based photodynamic therapy and glycated chitosan injection was been studied in the EMT6 mammary sarcoma and Line 1 lung adenocarcinoma mouse models, respectively. In each model, BALB/c mice were subcutaneously inoculated with $10^6$ viable tumor cells into the lower dorsal area. Tumors were treatment size (7 to 8 mm) after 7 days.

In the EMT6 mammary sarcoma model, treatment groups evaluated are detailed in the table below. Photofrin (Mont-Saint-Hilaire, Quebec, Canada) was prepared in 5% sterile dextrose to a 1 mg/mL concentration. A 5 mg/kg dose of photofrin was intravenously administered 24 h prior to irradiation. Animals were shielded from direct light immediately after the photosensitizer injection until 3 days after photodynamic treatment. Mice were restrained anaesthetized in holders exposing their backs during light treatment. Light (630 nm) was delivered through an 8 mm diameter liquid light guide. The power density was set at 100 mW/cm$^2$, for a total light dose of 60 J/cm$^2$. Immediately after light irradiation, if applicable, animals were administered a peritumoral dose of 0.5 or 1.5% glycated chitosan. Animals were observed for tumor emergence every 2 days up to 90 days after photodynamic treatment and changes in tumor volume was determined 3 times a week.

Survival Rates After Photofrin-Based Photodynamic and Glycated Chitosan Treatment in Mice Bearing EMT6 Mammary Tumors

| Treatment | Number of Mice | Number of Long-Term Surviving Mice | Long-term Survival Rate (%) |
|---|---|---|---|
| Control | 8 | 0 | 0.0 |
| Non-Thermal Laser Only | 8 | 0 | 0.0 |
| Non-Thermal Laser + 1.5% GC[a] | 8 | 0 | 0.0 |
| Non-Thermal Laser + Photofrin | 8 | 3 | 37.5 |

Survival Rates After Photofrin-Based Photodynamic and Glycated Chitosan Treatment in Mice Bearing EMT6 Mammary Tumors

| Treatment | Number of Mice | Number of Long-Term Surviving Mice | Long-term Survival Rate (%) |
|---|---|---|---|
| Non-Thermal Laser + Photofrin + 0.5% GC | 8 | 5 | 62.5 |
| Non-Thermal Laser + Photofrin + 1.5% GC | 8 | 6 | 75.0 |

$^a$ = It should be noted that the laser treatment did not result in heating the tumor because the light absorbing agent was not used nd the laser power was not sufficient to heat the tumor. Therefore, this group is not representative of the laser-assisted immunotherapy system.
GC = Glycated chitosan
Laser treatment with a fluence rate of 100 mW/cm$^2$ and a total light dose of 60 J/cm$^2$, 5 mg/kg photofrin was intravenousy administered 24 h prior to irradiation.
0.1 mL of 0.5% glycated chitosan was injected peritumorally immediately after irradiation.

All photodynamic and photodynamic glycated chitosan-treated rats had complete tumor regression by the day after treatment. Tumor reoccurrence was generally detected within 2 weeks after treatment. The efficacy of standard photodynamic therapy was 37.5%, which was increased following administration of 0.5 and 1.5% glycated chitosan with values of 82.5 and 75%, respectively. Glycated chitosan significantly increased survival rates in tumor-bearing mice compared to photodynamic treatment only (p<0.05).

In the Line 1 lung tumor model, treatment groups were as presented the table below. mTHPC was prepared in a 2:3:5 (v/v/v) mixture of ethanol, polyethyleneglycol 400, and water for a final 0.02 mg/mL concentration. A 0.1 mg/kg dose of mTHPC was intravenously administered 24 h prior to irradiation. Animals were shielded from direct light immediately after the photosensitizer injection until 3 days after photodynamic treatment. Mice were restrained anaesthetized in holders exposing their backs during light treatment. A 652 nm light from a 0.25 W diode laser was delivered through an 8 mm diameter liquid light guide. The power density was set at 110 mW/cm$^2$, fora total light dose of 30 J/cm$^2$. Immediately after light irradiation, if applicable, animals were administered a peritumoral dose of 1.67% glycated chitosan. Animals were observed for tumor emergence every 2 days up to 90 days after photodynamic treatment and 3 times a week changes in tumor size was determined.

Survival Rates After mTHPC-Based Photodynamic and Glycated Chitosan Treatment in Mice Bearing Line 1 Lung Tumors

| Treatment | Number of Mice | Number of Long-Term Surviving Mice | Long-term Survival Rate (%) |
|---|---|---|---|
| Control | 8 | 0 | 0.0 |
| Laser Treatment Only | 8 | 0 | 0.0 |
| Laser + GC | 8 | 0 | 0.0 |
| Laser + mTHPC | 8 | 0 | 0.0 |
| Laser + mTHPC + 1.67% GC | 8 | 3 | 37.5 |

GC = Glycated chitosan.
mTHPC = meso-substituted tetra (meta-hydroxy-phenyl) chlorin-based photodynamic therapy.
0.1 mg/kg mTHPC was intravenously administered 24 h prior to irradition.
0.09 mL of 1.67% glycated chitosan was injected peritumorally immediately after irradiation.

Figure 6:
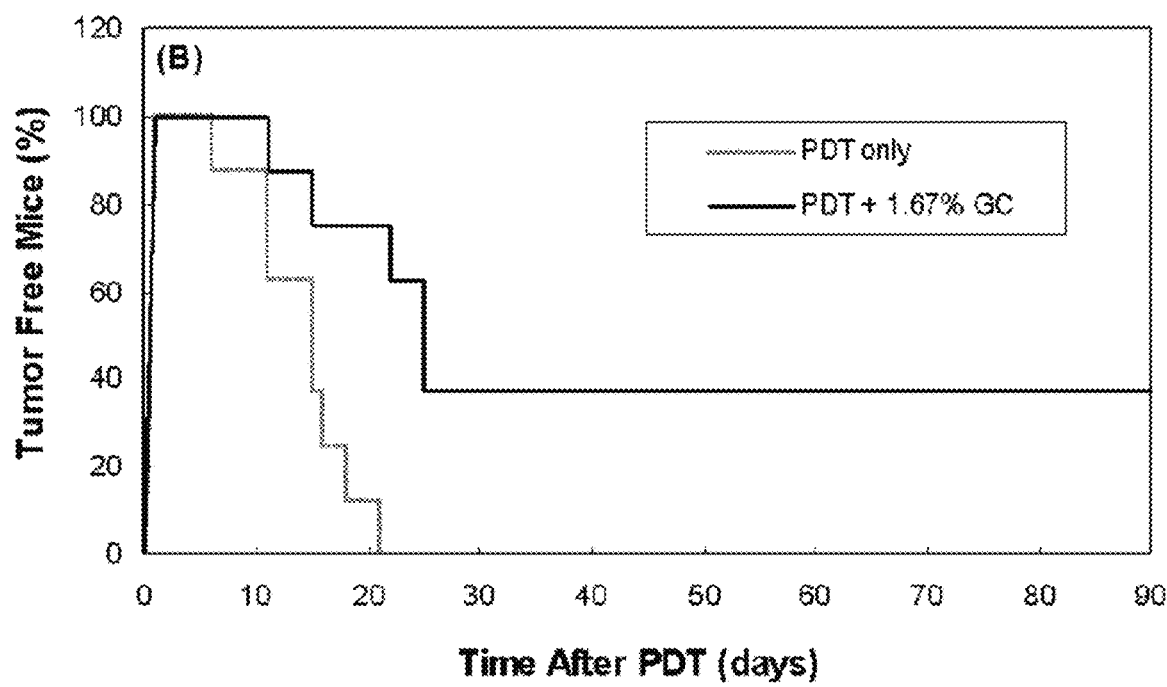
FIG. 6 depicts a graph that shows the effect of tumour-localized glycated chitosan treatment on the response to mTHPC-based PDT in mouse Line 1 tumors. In this graph: GC=Glycated chitosan; mTHPC=Meso-substituted tetra (meta-hydroxy-phenyl) chlorin; and PDT=Photodynamic therapy.

Tumor reoccurrences were observed in all mice within 3 weeks. Following mTHPC-based photodynamic therapy, administration of 1.67% glycated chitosan resulted in a 37.5% survival rate, while other combinations were not effective. The Line 1 lung tumor model was considered a poorly immunogenic tumor model. The effect of tumor-localized glycated chitosan treatment on the response of the mouse Line 1 tumors to mTHPC-based photodynamic therapy is presented in FIG. 6.

The results of these studies indicate that an active immunological stimulation is needed to augment the efficiency of phototherapy.

Example 11

Effect of Different Components of Laser-Assisted Immunotherapy in Treatment of Metastatic Tumors in Rats Various combinations of three components of the laser-assisted immunotherapy system were evaluated in this study utilizing female and male rats bearing metastatic breast and prostate tumors, respectively. The laser-assisted immunotherapy system consisted of a near-infrared laser diode laser with a maximum output of 25 W; the laser-absorbing dye, indocyanine green; and the immunoadjuvant, glycated chitosan. When the primary tumor was 0.2 to 0.5 cm$^3$, treatment was initiated in the tumor-bearing rats. A solution of 0.2 mL of GC and/or ICG was injected into the center of the primary tumor in all groups. In rats receiving laser treatment, the injections occurred 2 h before irradiation, with animals anesthetized and the hair overlaying the tumor clipped. The laser settings were 2 W and 10 min, with the laser fiber tip maintained a distance of 4 mm from the overlying skin and the laser energy directed to the treatment sites through optical fibers. The animals were individually housed following treatment. In the survival studies, the breast or prostate tumor-bearing rats were observed daily and the three dimensions of each tumor were measured weekly. Female Wistar Furth rats (5 to 6 weeks of age, 100 to 125 g) were subcutaneously inoculated with the DMBA-4 transplantable, metastatic mammary tumor (10$^5$ viable tumor cells) into one inguinal fat pad of each rat. The primary tumor emerged 7 to 10 days after inoculation. Metastatic tumors along the lymphatics and at remote sites usually became palpable in approximately 2 weeks. Without treatment, tumor-bearing rats have an average survival time of 35 days. Eight groups of metastatic breast tumor-bearing rats were treated with the different components of the laser-assisted immunotherapy system, as detailed in the table below. The survival rate and primary and metastatic tumor profiles were determined for the individual components and various combinations of the components. In addition, three groups of female rats (n=16/group) were treated with 0.5, 1.0, and 2.0% glycated chitosan to evaluate the impact of the immunoadjuvant concentration on rat survival.

Treatment Parameters of Different Laser-Assisted Immunotherapy Components in Female Metastatic Breast Tumor-Bearing Rats

| Group | Laser | Dye/Adjuvant | Number of Rats |
|---|---|---|---|
| Control | — | — | 35$^a$ |
| ICG Injection Only | — | 0.25% ICG$^b$ | 12 |
| GC Injection Only | — | 1.0% GC$^b$ | 12 |
| Laser Only | 2W, 10 min. | — | 12 |
| Laser + ICG | 2W, 10 min. | 0.25% ICG$^b$ | 12 |
| Laser + GC | 2W, 10 min. | 1.0% GC$^b$ | 12 |

Treatment Parameters of Different Laser-Assisted Immunotherapy
Components in Female Metastatic Breast Tumor-Bearing Rats

| Group | Laser | Dye/Adjuvant | Number of Rats |
|---|---|---|---|
| ICG + GC | — | 0.25% ICG/1.0% GC[b] | 12 |
| Laser + ICG + GC | 2W, 10 min. | 0.25% ICG/1.0% GC[b] | 31[a] |

Figure 7A:
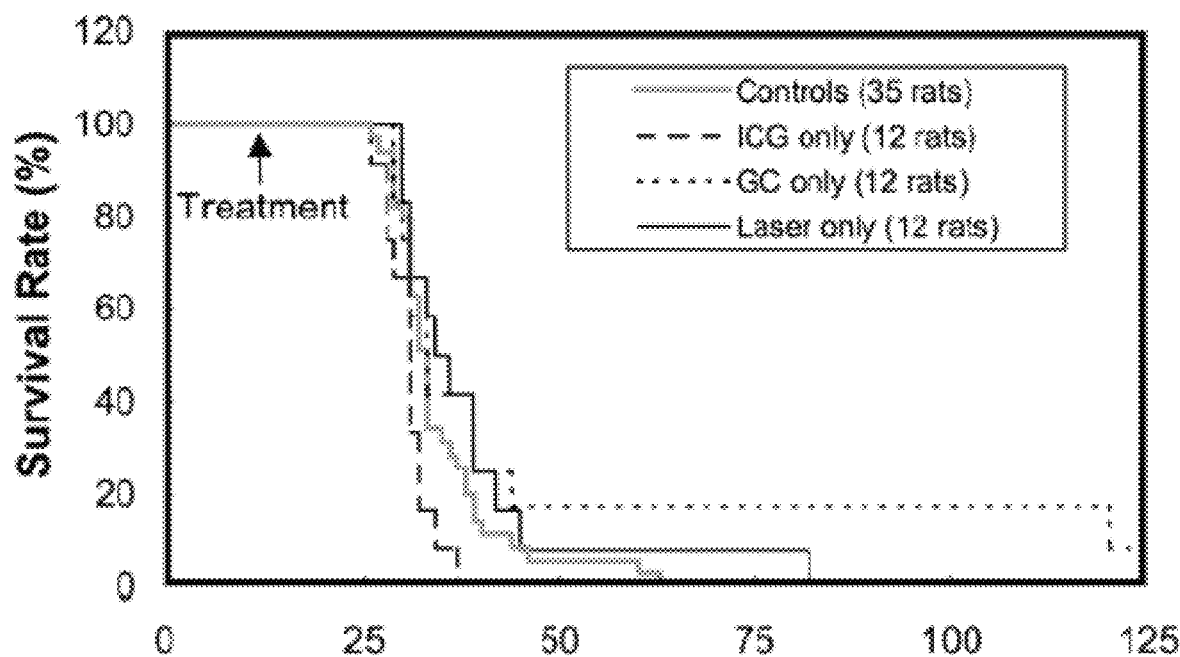
FIGS. 7A-7C depict graphs that show rat survival rates following treatment with one, two, or three components of the laser-assisted immunotherapy system. In these graphs, GC=1.0% glycated chitosan; and ICG=0.25% indocyanine green.
Figure 7B:
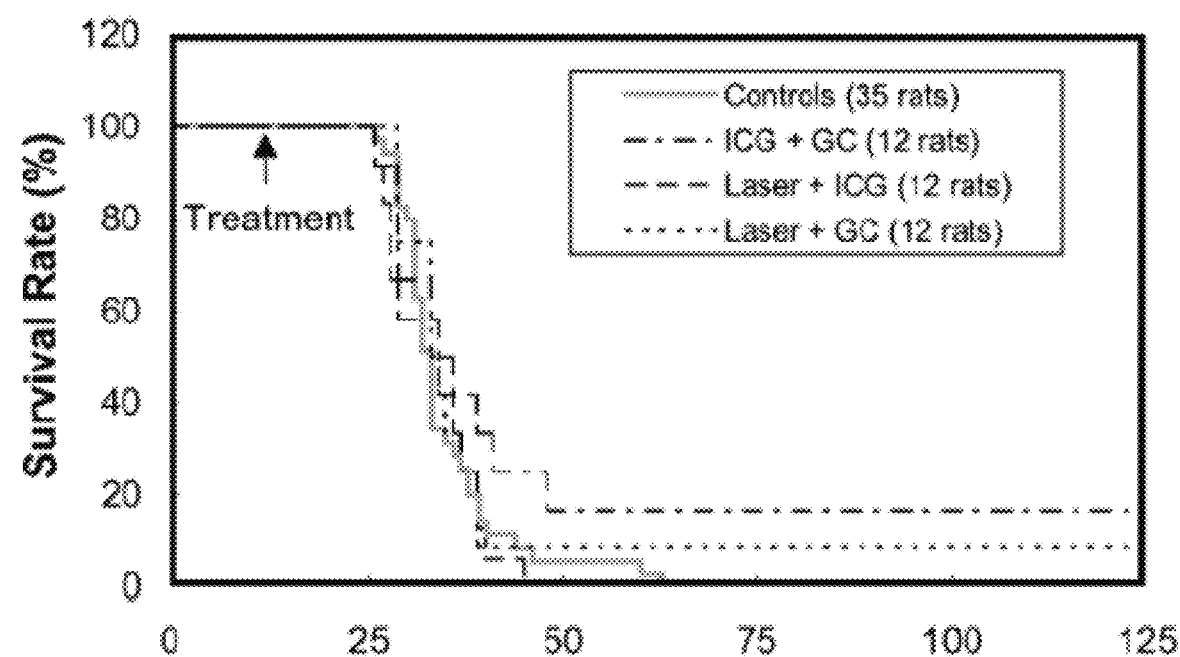
Figure 7C:
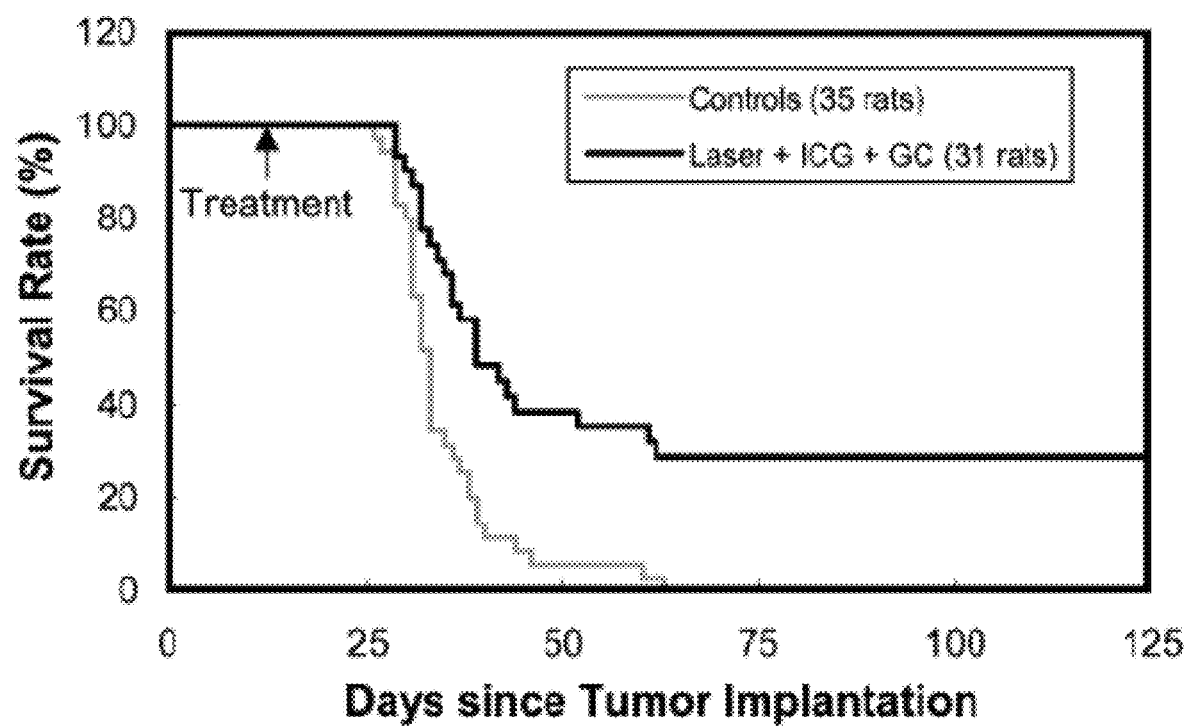

[a] = Data collected from 2 separate experiments
[b] = The injection volume (.0.2 mL) was injected directly to the center of the primary tumor
GC = Glycated chitosan
ICG = Indocyanine green
— = Not applicable In the metastatic breast tumor-bearing rats, single component treatment resulted in all rats in the indocyanine green and laser-only groups dying, with average survival times similar to the control group. Two rats in the glycated chitosan group survived, with one rat considered a long-term survivor and the other rat considered a prolonged survivor (>120 days). Following treatment with two components, 1 and 2 long-term survivors were observed in the laser plus glycated chitosan and indocyanine green plus glycated chitosan groups, respectively. There was no statistical significance in the survival time when the single- or two-component treatment groups were compared to the control group. Nine rats had long-term survival after the three-component laser-assisted immunotherapy (i.e., photothermal application combined with glycated chitosan) treatment, resulting in an approximate 30% cure rate in two separate experiments of 31 rats. A significant difference ($p<0.0001$) in median survival time of the treated rats was observed compared to the control rats. The survival rate of rats following the treatment with one, two, or three components of the laser-assisted immunotherapy system is presented in FIGS. 7A-7C. Metastatic tumors usually emerged 2 weeks after the inoculation of the primary tumor and reached a peak size before the regression.

Example 12

Antitumor Immunity Induced by Laser-Assisted Immunotherapy and its Adoptive Transfer To investigate the mechanism of the antitumor immunity induced by laser-assisted immunotherapy, adoptive transfer using immune spleen cells was performed. Female Wistar Furth rats were subcutaneously inoculated with the DMBA-4 transplantable, metastatic mammary tumor ($10^6$ viable tumor cells) into one inguinal fat pad of each rat, 7 to 10 days prior to laser-assisted immunotherapy treatment. Without treatment, tumor-bearing rats survived an average of approximately 30 days. Laser treated rats were administered 0.2 mL of a solution containing both 0.25% indocyanine green and 1% glycated chitosan directly into the primary tumor before laser treatment. An 805 nm laser at 2 W for 10 min was used for irradiation. The protective ability of induced immunity was evaluated in several groups of successfully treated tumor-bearing rats that were challenged repeatedly with increased inoculation doses of viable tumor cells. In addition, resistance to tumor challenges after laser-assisted immunotherapy and the inhibition of tumor growth were evaluated in naive rats.

Fifteen rats that had been successfully treated by laser-assisted immunotherapy were rechallenged with $10^6$ viable tumor cells 120 days after initial inoculation. Eighteen naive age-matched rats (25 weeks of age) were inoculated with $10^6$ viable tumor cells for comparative purposes. All of the successfully treated rats showed total resistance to the challenge, with neither primary tumors nor metastasis observed; however, the age-matched control rats developed primary and metastatic tumors and died within 30 days after inoculation. A separate group of young rats (approximately 8 weeks of age) were inoculated with $10^5$ viable tumor cells. Survival appeared to be dependent on the tumor dose, with control rats inoculated with $10^6$ and $10^6$ viable tumor cells surviving on average 33 and 28 days, respectively. Successfully treated rats usually experienced a gradual regression in both treated primary tumor and untreated metastasis.

After the first rechallenge, the rats from several experimental groups were followed by two subsequent challenges in a time interval from 1 to 5 months, with the $10^6$ viable tumor cells. The rats successfully treated by laser-assisted immunotherapy were totally refractory to three tumor challenges. This data is presented in the table below. In contrast, the age-matched control tumor-bearing rats developed multiple metastases in remote inguinal and axillary areas and died within 35 days. Multiple metastases developed in all 20 control rate inoculated with $10^5$ viable tumor cells; however, these rats had a slightly increased survival time compared with the age-matched control rats that were inoculated with the higher 10V viable tumor cell dose. The resistance to tumor rechallenge in successfully treated rats strongly suggests tumor-selective immunity.

Treatment Parameters of Different Laser-Assisted Immunotherapy
Components in Female Metastatic Breast Tumor-Bearing Rats

| Group | Number of Rats | Number of Tumor Cells | Tumor Rate | Death Rate 30 Days | Death Rate 40 Days | Survival (Days) |
|---|---|---|---|---|---|---|
| Cured Rats[a] | 15 | $10^6$ | 0% | 0% | 0% | >120 |
| Cured Rats[b] | 15 | $10^6$ | 0% | 0% | 0% | >120 |

Treatment Parameters of Different Laser-Assisted Immunotherapy
Components in Female Metastatic Breast Tumor-Bearing Rats

| Group | Number of Rats | Number of Tumor Cells | Tumor Rate | Death Rate 30 Days | Death Rate 40 Days | Survival (Days) |
|---|---|---|---|---|---|---|
| Cured Rats[c] | 15 | $10^6$ | 0% | 0% | 0% | >120 |
| Age-Matched Tumor Control Rats[d] | 18 | $10^6$ | 100% | 83% | 100% | 28.2 +/− 2.8 |
| Young Tumor Control Rats[e] | 20 | $10^6$ | 100% | 20% | 100% | 32.7 +/− 3.5 |

[a]= First challenge. Tumor-bearing rats cured by laser-assisted immunotherapy, rechallenged with viable tumor cells 120 days after the initial inoculation
[b]= Second challenge. Tumor-bearing rats cured by laser-assisted immunotherapy, rechallenged with viable tumor cells a second time after the first challenge.
[c]= Third challenge. Tumor-bearing rats cured by laser-assisted immunotherapy, rechallenged with viable tumor cells a third time after the second challenge.
[d]= Untreated rats the same age as the cured rats at time of inoculation (no previous tumor exposure)
[e]= Untreated rats that were 8 weeks of age at the time of inoculation (no previous tumor exposure)

Figure 8:
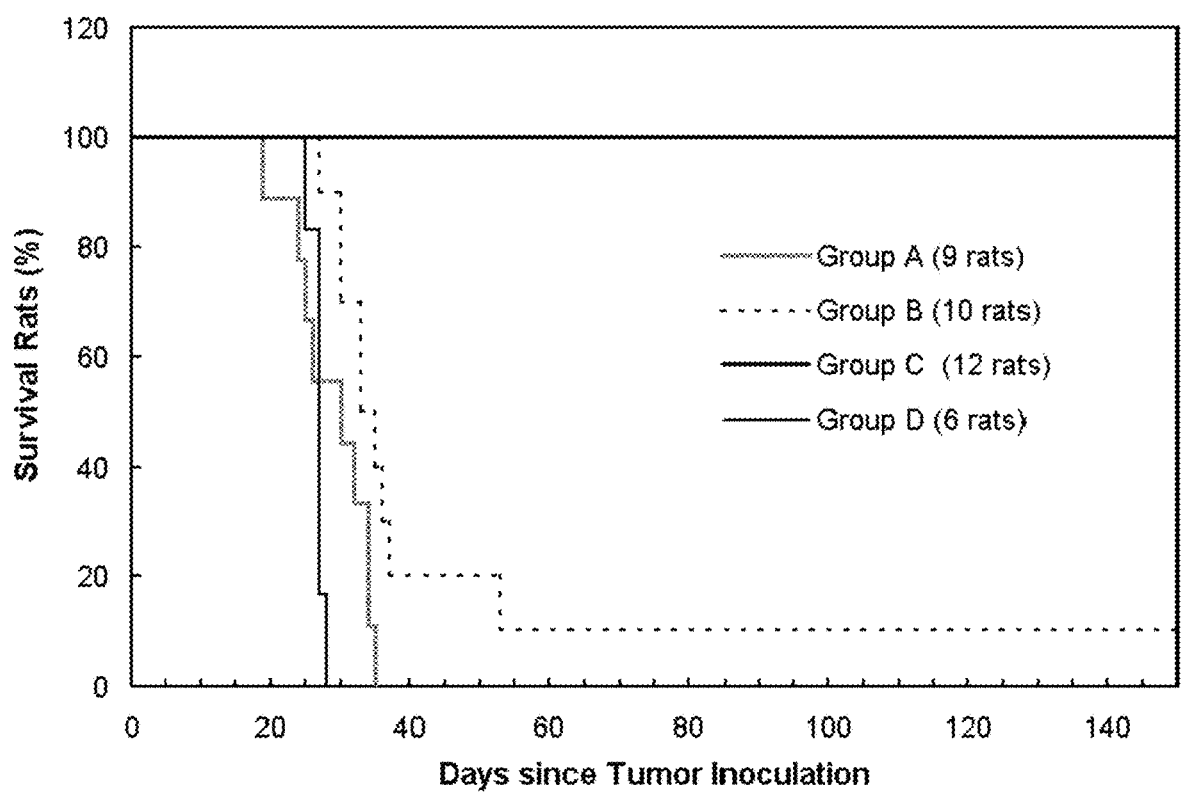
FIG. 8 depicts a graph that shows rat survival curves in the adoptive immunity transfer experiments using rat splenocytes as immune cells. In this graph, Group A=Results from tumor control rats; group B=Results from rats injected with tumor cells admixed with spleen cells from an untreated tumor-bearing rat; Group C=Results from rats injected with tumor cells admixed with spleen cells from laser-assisted immunotherapy successfully treated rat; Group D=Results using spleen cells from a naïve rate. Note: Data collected from 2 separate experiments were combined and plotted together.

For the adoptive immunization experiment, viable tumor tissue harvested from live DMBA-4 tumor-bearing rats was dispersed to a single-cell suspension by grinding in a loose-fitting ground glass homogenizer. The long-surviving rats were sacrificed 28 days after tumor rechallenge with the $10^6$ viable tumor cells, and their spleens were dissected free of fat. Two separate experiments were conducted using the splenocytes from control tumor-bearing rats. The spleen cells were harvested 22 and 39 days after tumor inoculation in the first and second experiment, respectively. Cell suspensions were prepared by mechanical disruption into medium with 10% fetal calf serum. Spleen cells were also collected from a naive rat without prior exposure to the tumor cells. Spleen cells and viable tumor cells were counted on a hemocytometer before mixing to a 400:1 spleen:tumor cell ratio. Naive rats were inoculated with the mixture containing $4 \times 10^7$ spleen cells and $10^5$ viable tumor cells in a volume of 0.2 mL. For the adoptive immunity transfer experiments, 4 groups of naive female Wistar Furth rats were inoculated with tumor cells. The treatment groups were Group A tumor-bearing control rats inoculated with $10^5$ viable tumor cells without treatment; Group B rats inoculated with the tumor cells mixed with the spleen cells from a control tumor-bearing rat; Group C rats inoculated with the tumor cells mixed with the spleen cells from a tumor-bearing rat successfully treated by laser-assisted immunotherapy, 28 days after tumor rechallenge; and Group D rats inoculated with the tumor cells mixed with the spleen cells from a naive rat without prior tumor exposure. The experiment was performed in duplicate and the survival of rats from both experiments was combined and is presented in FIG. 8. There were no primary or metastatic tumors observed in Group C rats indicating that the spleen cells from laser-assisted immunotherapy successfully treated rats by providing 100% protection to the recipients. Multiple metastases and death within 35 days of tumor inoculation were observed in all Group A tumor-bearing control rats. There was no protection provided by the spleen cells from a healthy rat in Group D. A single rat out of 10 rats in Group B survived; however, this rat later developed both primary tumor and metastases. All Group C rats were rechallenged 60 days after the adoptive immunity transfer, and all withstood the challenge. The immune spleen cells of the rats in Group C were collected and mixed with tumor cells in the same ratio as in the first adoptive transfer to evaluate the ability of these animals' spleen cells in protecting a subsequent cohort of normal Wistar Furth recipient rats (n=6) that were inoculated with this admixture. The immune cells from the Group C rats protected 5 of 6 naive rats, as neither primary nor metastatic tumors were observed. The rat that died had a prolonged survival time (60 versus 30 days) and a delayed tumor emergence after inoculation (37 versus 7 to 10 days), in comparison with the control group.

The resistance of successfully treated rats when tumor rechallenged strongly suggests that the tumor-selective immunity has a long-lasting effect.

Example 13

Combination of Laser-Assisted Immunotherapy and Low-Dose Chemotherapy

In one exemplary clinical study, two breast cancer patients received cyclophosphamide weekly (after inCVAX treatment) at a dose of between 150 and 200 mg/m². The patients initially responded well to the treatment with tumor shrinkage and minimal adverse reactions. After a few months the response slowed, so the oncologist changed the low-dose chemotherapy to a weekly regimen of Paclitaxel at 75 mg/m², and again the response was very good with shrinking tumors. No new metastases appeared. The patients continued to receive the low dose chemotherapy. A third patient became operable following the low dose chemotherapy, and a mastectomy was performed, so a combination with surgery was also an option.

Example 14

Demonstration of the Sterile Filterability of IP-001

IP-001 is an illustrative embodiment of Glycated Chitosan (GC), which is a semi-synthetic glucosamine-based polymer. IP-001 is a novel and unobvious GC. Specifically, the data below supports the advantageous and unexpected properties of IP-001 with respect to its ability to be manufactured in a consistent and compliant manner. The IP-001 is formulated as a 1.0% solution (w/w) in water buffered to pH of 5.5 and has a viscosity of 50-60 cPs and is meant for intratumoral injection. IP-001 is a variant of GC and has the following molecular characteristics:

Weight Averaged Molecular Weight (Mw) of ~250 kDa
Degree of Deacetylation (DDA) of ~80%
Degree of Glycation (DoC) of ~5%

One of the main advantages exhibited by IP-001 is its ability to be sterile filtered. The sterile filtration of pharmaceutical solutions is an industry standard for ensuring patient safety. Specifically, in the area of sterile injectable solutions, sterile filtration is often the favored method for sterilization, as it is an easily scalable process and does not affect the chemical structure of the active pharmaceutical ingredient (API) as often occurs during autoclave- or gamma irradiation-based sterilizations. Additionally, sterile filtration offers cost advantages in the development, validation and execution of the process, relative to autoclave and gamma sterilization. The sterile filtration of solutions of polymers adds an additional degree of complexity, as physiochemical properties, such as viscosity can often slow or stop the filtration process. Therefore, the conditions of the filtration as well as the chemical and physiochemical characteristics of the polymer must be considered carefully.

With respect to IP-001, it was unexpectedly discovered that the specific embodiment in conjunction with a formulation including defined ranges of concentration and pH were needed to successfully sterile filter the formulation and provide a compliant and consistent drug product. As shown below, the results of our experiments demonstrate the filterability compared to embodiments of GC that are outside of the preferred ranges, described above and specifically include those with a molecular weight of less than 500,000 Daltons.

It should be noted that the state of the art, an example of which being Mirko Weinhold's published PhD thesis entitled: "Characterization of Chitosan using Triple Detection size-exclusion chromatography and $^{13}C$ NMR spectroscopy" at the Center for Environmental Research and Sustainable Technology, University Bremen, October 2010), teaches that chitosan viscosity increases in a linear fashion as the molecular weight of the GC increases. Indeed, we discovered unexpectedly after many years of trial and error that the prior art teachings, if followed, do not provide sufficient guidance which would lead one to conclude that particle size correlates to molecular weight (see specifically the data presented below).

Under current regulatory and scientific standards, pharmaceutical solutions can be considered sterile following the filtration through a filter with an effective pore-size of 0.22 microns or smaller. Additionally, the process and materials must be tested and validated in a GMP-compliant manner. The sterile filtration of IP-001 drug product has been carefully studied. The full-scale process for the sterilization of IP-001 utilizes Pall Corporations Flurodyne capsule filters (part #KA2DFLP1S) in a redundant (serial) manner. The filter chosen meets all regulatory requirements and is chemically compatible with IP-001. Additionally, a product-specific validation of the process (Study #-VAL-AM-000754-B) was carried out. As part of this study, IP-001 drug product demonstrated multiple times its ability to effectively undergo sterile filtration.

Referring to FIG. 9 (recirculation data for IP-001 Drug Product), the data clearly shows that when IP-001 drug product is recirculated through sterilizing-grade membranes for up to 3 hours at a constant pressure there is minimal loss in flow rate (indicating minimal fowling or clogging of the filter). This test represents an extreme stressing of the system, as sterile filtration in practice is only a single our double pass and not a continuous recirculation of the solution through the membrane. This data strongly supports the fact that IP-001 Drug Product can be filter sterilized with little to no loss in integrity of the polymer solution.

The process validated by Pall Corporation in Study VAL-AM-000754-B was subsequently performed on scale multiple time. In one example, the production of GMP-grade IP-001 Drug Product, the following data was collected:

Pre-filtration weight of IP-001 Drug Product—7.602 kg
Time for redundant sterile filtration—3 hours
Post-filtration weight of IP-001 Drug Product—7.384 kg
Yield of filtration—97.1% in order to demonstrate of the advantage of IP-001 over other less preferred GC embodiments with respect to sterile filtration, a direct comparison of sterile filtration of IP-001 and larger Mw (500 kDa) GC was performed.

Comparison with Song et al. (Immunopharmacology and Immunotoxicology, 2009; 31 (2), 202-208)

A 1% solution of GC with a Mw of approximately 500 kDa was synthesized as described in Song, et. al. Song describes a sterilization by autoclave, and it was the opinion of Immunophotonics that this process would in fact affect the MW of the polymer. To test this, solutions of 500 kDa GC were tested for their abilities to be sterile filtered both before and after the reported autoclave sterilization and compared to that of IP-001 Drug Product.

Figure 10:
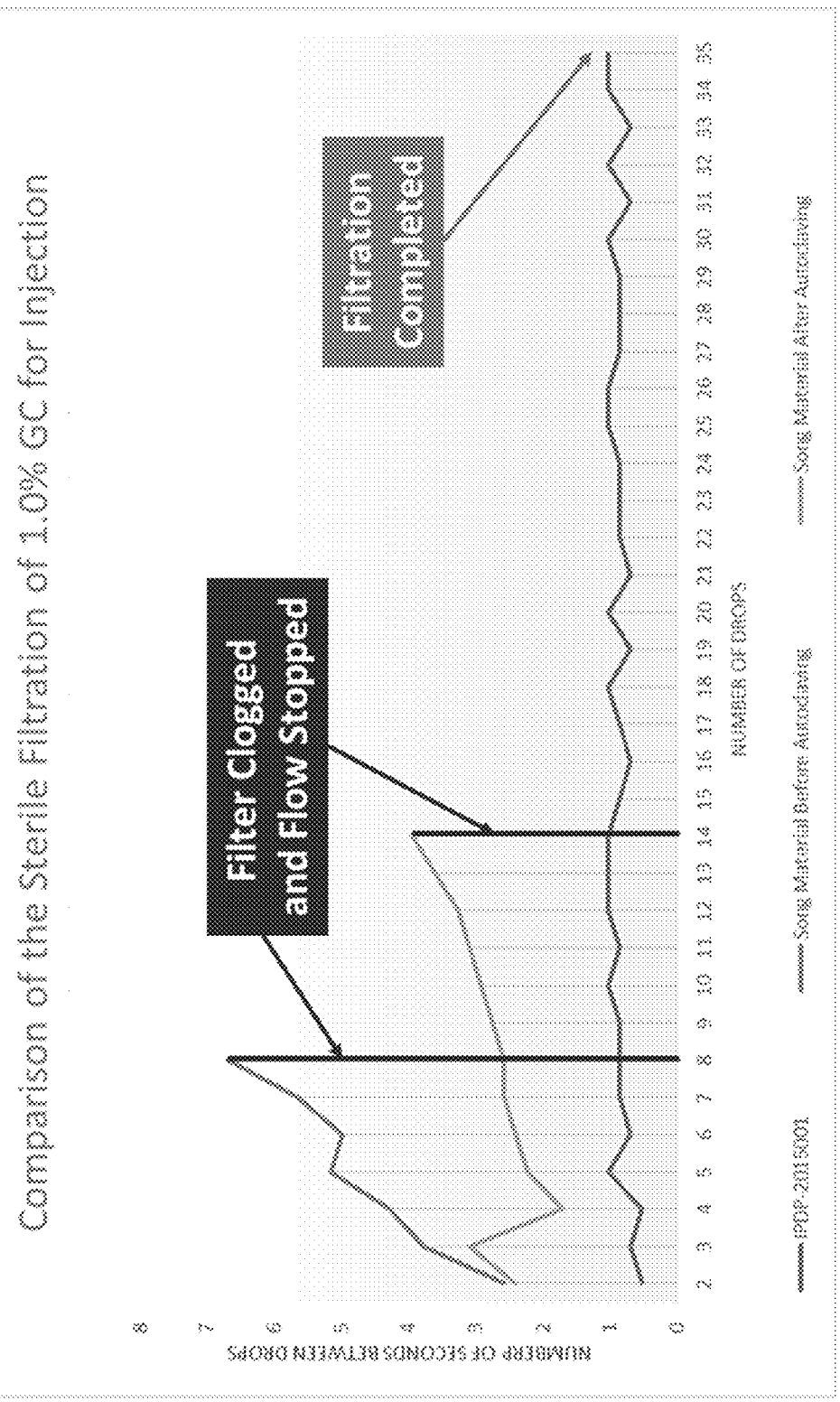
FIG. 10 is a graph showing comparative filtration rate data for various 1% solutions of GC.

Referring now to FIG. 10, which shows filtration rate data for various 1% solutions of GC. In order to generate the data in FIG. 10, 1 mL of each solution was added to a 2.5 mL syringe fitted with a luer-fitted digital pressure sensor. A small scale, representative sterile filter with a luer fitting was then attached to the outlet of the pressure sensor. The solutions were forced through the filters keeping the pressure between 500 and 600 psi. The resulting drop-rate was measured.

The data in FIG. 10 clearly shows that the IP-001 drug product (lot IPDP-2015001) maintained a consistent flow rate until all the solution had been pushed through the filter. In contrast, the pre- and post-autoclave solutions of 500 kDa GC exhibited steadily decreasing drop rates, both ultimately clogging the filters and thus halting the filtration. Additionally, the data corresponds with the hypothesis that autoclaving reduces the molecular weight, as shown by the lower pressures and improved flows for autoclaved materials when compared to non-autoclaved material.

Figure 11:
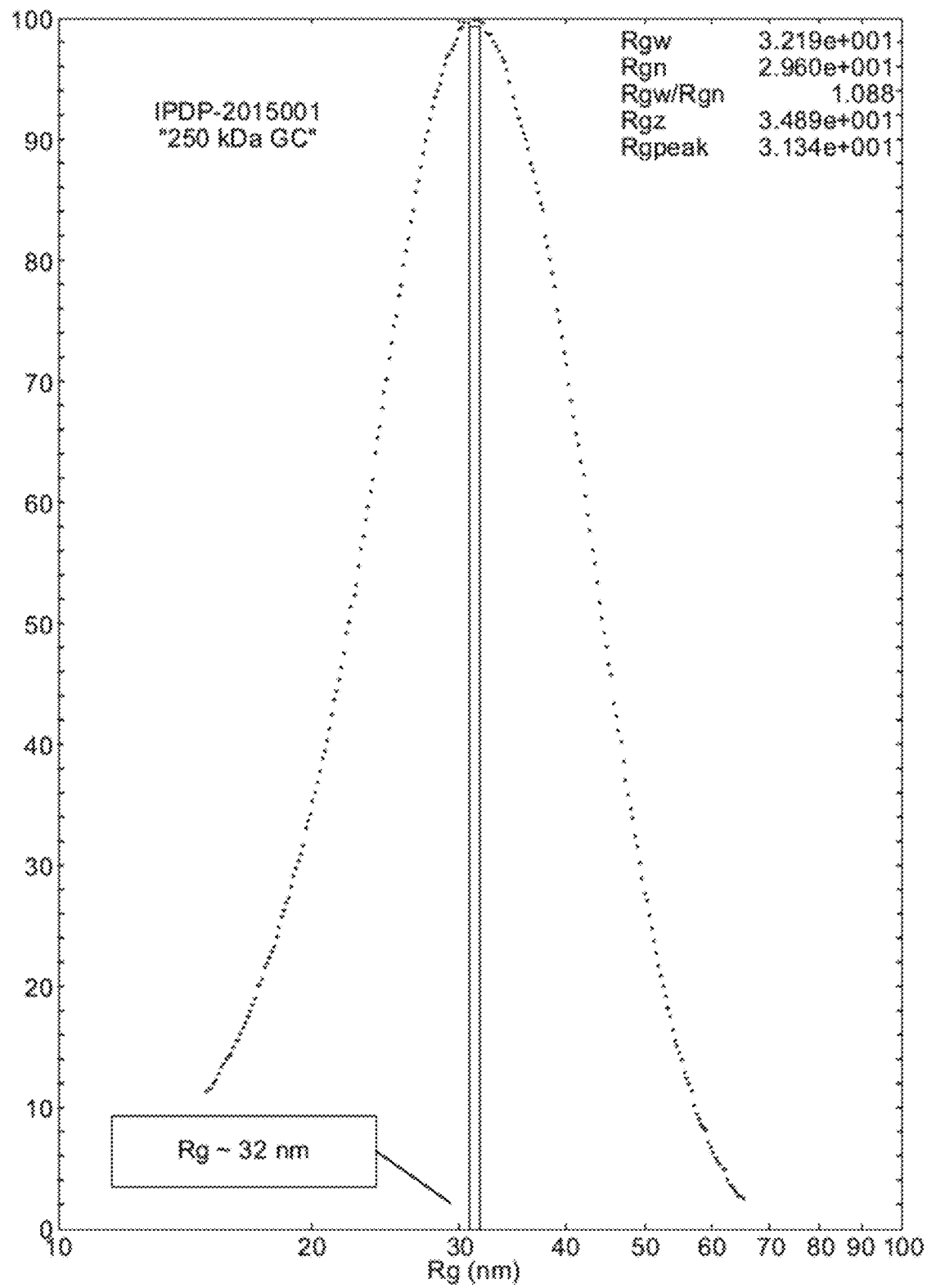
FIG. 11 illustrates particle size data for three GC solutions.
Figure 11:
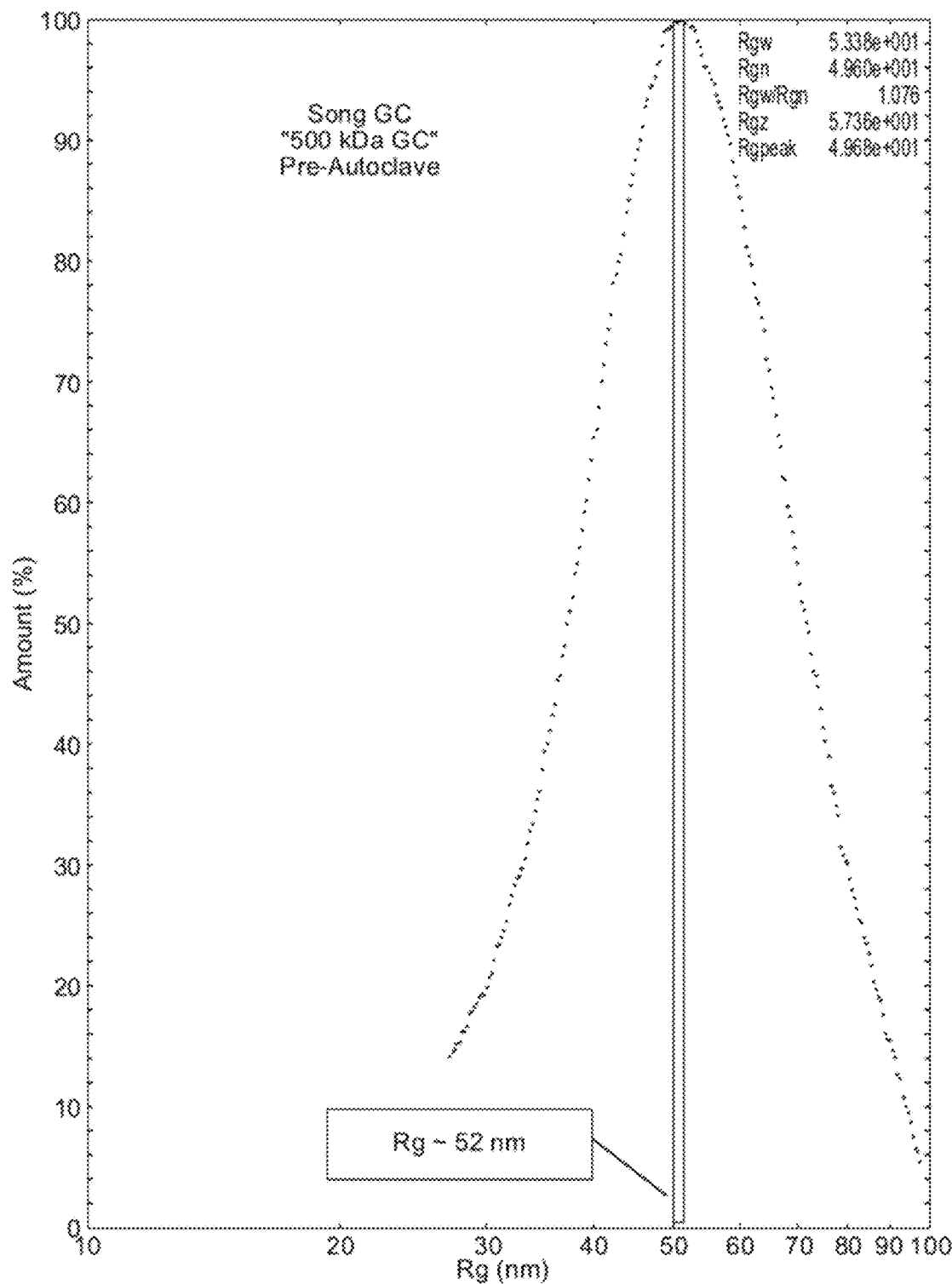
Figure 11:
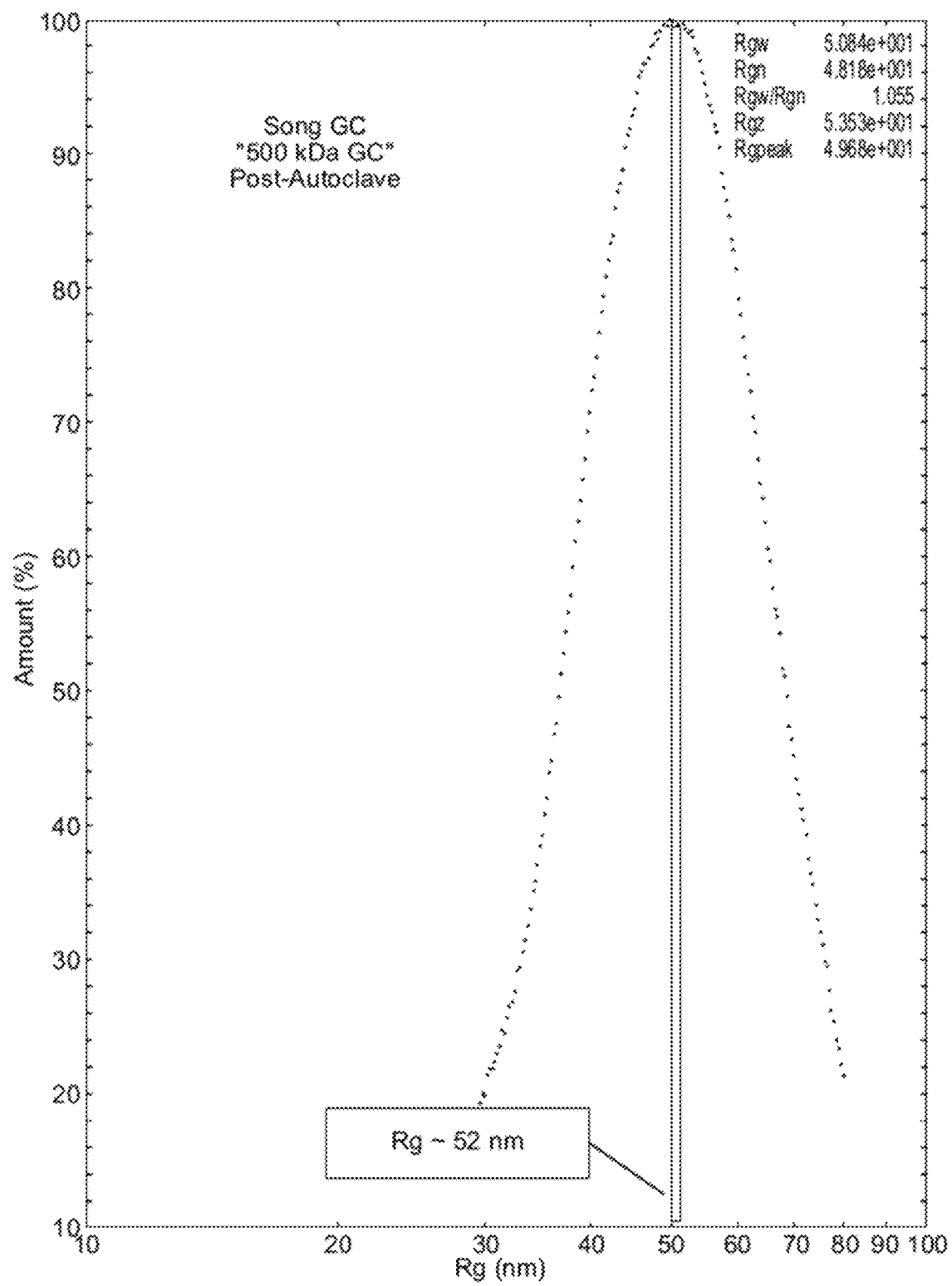

Referring now to FIG. 11, particle size data was collected for the 3 samples tested. A convenient estimate of particles sizes for chitosan solutions is the radius of gyration (Rg). While Rg is not the exact radius of the particle, more often than not, it is only slightly less than the radius of the particle. The data collected for the Rg of the GC solutions provides an explanation for their observed behavior in the filtration experiments. The radius of gyration for IP-001 Drug Product was measured to be ~32 nm while both solutions of the Song 500 kDa GC exhibited Rg's of ~52 nm. When the larger end of the polymer range is considered, it becomes evident why the material taught by Song et al. would not sterile filter, as the particles are approaching or larger than the effective pore size of the sterilizing filter.

In conclusion, the data described herein clearly demonstrates the advantage of the new and unobvious IP-001 with respect to its sterile filterability when compared to the GC reported by Song et al. and by extension, GC's of larger molecular weights. Additionally, and unexpectedly, IP-001 represents an optimal form of GC for sterile filtration. It is known that lowering the pH of solutions of chitosan increases the Rg while increasing the pH of GC solutions causes the material to crash out of solution (i.e. precipitate). Therefore, it was unexpectedly discovered altering the pH of larger GC molecules would not allow for sterile filtration. The data described herein and the additional development work performed for IP-001 clearly support that the described embodiment represents and clear and unexpected advantage when compared to the prior art.

Other Embodiments

From the foregoing description, it will be apparent to one of ordinary skill in the art that variations and modifications may be made to the embodiments described herein to adapt it to various usages and conditions.

We claim:

1. A method of treating a cancer in a patient in need thereof, comprising administering by injection a pharmaceutical formulation comprising a glycated chitosan to the patient, wherein: the glycated chitosan has a molecular weight of about 100,000 to about 300,000 Daltons; the glycated chitosan has a degree of deacetylation of about 75% to about 99%; and the glycated chitosan has a degree of glycation of free amino groups of about 0.1% to about 30%.

2. The method of claim 1, wherein the cancer comprises a neoplasm.

3. The method of claim 2, wherein the pharmaceutical formulation is administered into the neoplasm.

4. The method of claim 3, wherein the method comprises ablating the neoplasm.

5. The method of claim 1, wherein the cancer is a solid tumor cancer.

6. The method of claim 2, wherein the cancer is metastatic.

7. The method of claim 1, wherein the glycated chitosan has a molecular weight of about 250,000 Daltons.

8. The method of claim 1, wherein the glycated chitosan has a degree of deacetylation of about 80%.

9. The method of claim 1, wherein the degree of glycation is about 2%, about 7%, or about 12.5%.

10. The method of claim 1, wherein the pharmaceutical formulation comprises about 0.5%, about 1%, or about 1.5% by weight of the glycated chitosan.

11. The method of claim 10, wherein the pharmaceutical formulation comprises about 1% by weight of the glycated chitosan.

12. The method of claim 1, wherein the pharmaceutical formulation is sterile filtered.

13. A method of generating an in situ autologous vaccine, comprising: ablating a neoplasm in a host, thereby releasing fragmented neoplastic tissue and cellular molecules; and introducing by injection a pharmaceutical formulation comprising a glycated chitosan into the neoplasm, wherein: the glycated chitosan has a molecular weight of about 250,000 Daltons; the glycated chitosan has a degree of deacetylation of about 80%; and the glycated chitosan has a degree of glycation of free amino groups of about 2%, about 7%, or about 12.5%.

14. The method of claim 13, wherein the neoplasm is a cancer is a solid tumor cancer.

15. The method of claim 14, wherein the cancer is metastatic.

16. The method of claim 13, wherein the pharmaceutical formulation comprises about 0.5%, about 1%, or about 1.5% by weight of the glycated chitosan.

17. A method of enhancing immune system response to an antigen in a patient in need thereof, comprising administering a pharmaceutical formulation comprising a glycated chitosan to a patient, wherein: the glycated chitosan has a molecular weight of about 250,000 Daltons; the glycated chitosan has a degree of deacetylation of about 80%; and the glycated chitosan has a degree of glycation of free amino groups of about 2%, about 7%, or about 12.5%.

18. The method of claim 17, wherein the antigen is a tumor antigen.

19. The method of claim 18, wherein the tumor is a solid tumor cancer.

20. The method of claim 17, wherein the antigen is an infectious agent antigen.

21. The method of claim 17, wherein the pharmaceutical formulation comprises about 0.5%, about 1%, or about 1.5% by weight of the glycated chitosan.

* * * * *